US010345582B2

(12) United States Patent
Schneider et al.

(10) Patent No.: US 10,345,582 B2
(45) Date of Patent: Jul. 9, 2019

(54) MICROSURGERY SYSTEM FOR DISPLAYING IN REAL TIME MAGNIFIED DIGITAL IMAGE SEQUENCES OF AN OPERATED AREA

(71) Applicant: Elbit Systems Ltd., Haifa (IL)

(72) Inventors: Ron Schneider, Haifa (IL); Abraham Zeitouny, Haifa (IL)

(73) Assignee: ELBIT SYSTEMS LTD., Haifa (IL)

(*) Notice: Subject to any disclaimer, the term of this patent is extended or adjusted under 35 U.S.C. 154(b) by 612 days.

(21) Appl. No.: 14/642,201

(22) Filed: Mar. 9, 2015

(65) Prior Publication Data
US 2015/0173846 A1 Jun. 25, 2015

Related U.S. Application Data

(63) Continuation-in-part of application No. PCT/IL2013/050764, filed on Sep. 10, 2013.

(30) Foreign Application Priority Data

Sep. 10, 2012 (IL) .......................................... 221863

(51) Int. Cl.
A61B 1/00 (2006.01)
A61B 5/00 (2006.01)
(Continued)

(52) U.S. Cl.
CPC ........ *G02B 27/0101* (2013.01); *A61B 1/0005* (2013.01); *A61B 1/00009* (2013.01);
(Continued)

(58) Field of Classification Search
CPC ............ G02B 2027/013; G02B 27/017; G02B 27/0172; G02B 2027/0118;
(Continued)

(56) References Cited

U.S. PATENT DOCUMENTS 8,824,779 B1* 9/2014 Smyth .................. G06K 9/0061
382/100
2002/0082498 A1* 6/2002 Wendt ................. G06F 19/3406
600/411
(Continued)

FOREIGN PATENT DOCUMENTS

JP 2002-085330 A 3/2002
WO 2009/094646 A2 7/2009
WO WO 2011/142165 11/2011

OTHER PUBLICATIONS

Clarence E. Rash et al.: "Helmet-Mounted Displays: Sensation, Perception and Cognition Issues"; U.S. Army Aeromedical Research Laboratory, 2009 (971 pages).
(Continued)

Primary Examiner — Haixia Du
(74) Attorney, Agent, or Firm — Merchant & Gould P.C.

(57) ABSTRACT

A system captures and displays video of surgeries. The system may include at least one digital image sensor optically coupled to one or more lenses and configured to capture a video sequence of a scene in a surgery; at least one interface configured to receive at least one region on interest (ROI) of the captured video sequence; an electronic display, selected so that at least one of the digital image sensors has a pixel resolution which is substantially greater than the pixel resolution of the electronic display; and a computer processor configured to: receive the at least one captured video sequence and the at least one received ROI and display over the at least one electronic display a portion of the captured video sequence based on the at least one selected ROI.

30 Claims, 14 Drawing Sheets

(51) Int. Cl.

| | |
|---|---|
| *A61B 5/11* | (2006.01) |
| *A61B 17/00* | (2006.01) |
| *A61B 90/00* | (2016.01) |
| *A61B 90/20* | (2016.01) |
| *A61B 90/30* | (2016.01) |
| *A61B 90/50* | (2016.01) |
| *G02B 27/00* | (2006.01) |
| *G02B 27/01* | (2006.01) |

(52) U.S. Cl.
CPC ...... *A61B 1/00039* (2013.01); *A61B 1/00193* (2013.01); *A61B 5/0066* (2013.01); *A61B 5/748* (2013.01); *A61B 90/30* (2016.02); *A61B 90/37* (2016.02); *G02B 27/017* (2013.01); *G02B 27/0172* (2013.01); *A61B 5/1114* (2013.01); *A61B 90/20* (2016.02); *A61B 2017/00216* (2013.01); *A61B 2090/365* (2016.02); *A61B 2090/367* (2016.02); *A61B 2090/368* (2016.02); *A61B 2090/371* (2016.02); *A61B 2090/372* (2016.02); *A61B 2090/373* (2016.02); *A61B 2090/502* (2016.02); *A61B 2576/00* (2013.01); *G02B 27/0093* (2013.01); *G02B 2027/014* (2013.01); *G02B 2027/0138* (2013.01); *G02B 2027/0141* (2013.01); *G02B 2027/0147* (2013.01); *G02B 2027/0187* (2013.01); *G05B 2219/35503* (2013.01)

(58) Field of Classification Search
CPC ............. G01N 33/5011; G01N 33/502; G06K 9/00127; A61B 17/128
USPC ......................................................... 345/660
See application file for complete search history.

(56) References Cited

U.S. PATENT DOCUMENTS

| | | | |
|---|---|---|---|
| 2005/0107808 A1* | 5/2005 | Evans ................... | A61B 34/32 606/139 |
| 2009/0245600 A1 | 10/2009 | Hoffman et al. | |
| 2012/0062769 A1* | 3/2012 | Kinoshita ................ | G03B 5/00 348/240.2 |
| 2012/0200700 A1* | 8/2012 | Bennett ................... | G01S 17/42 348/143 |
| 2012/0212484 A1* | 8/2012 | Haddick ............ | G02B 27/0093 345/419 |
| 2013/0113973 A1* | 5/2013 | Miao ...................... | G09G 3/003 348/333.01 |
| 2013/0335404 A1* | 12/2013 | Westerinen ............ | G06F 3/033 345/419 |
| 2014/0340287 A1* | 11/2014 | Achilefu ................ | A61B 19/56 345/8 |

OTHER PUBLICATIONS

Walter J. Greenleaf, PhD; "Medical Applications of Virtual Reality"; Overview, Feb. 2004 (21 pages).
Office Action issued in Israeli Patent Application No. 221863, dated Feb. 17, 2013.
International Search report for International Application No. PCT/IL2013/050764 dated Jul. 4, 2014 (4 pages).
Office Action for European Patent Application No. 13785660.5, dated Feb. 13, 2018.
Office Action for European Patent Application No. 13785660.5, dated Jul. 5, 2017.
W. Birkfellner et al., "A Head-Mounted Operating Binocular for Augmented Reality Visualization in Medicine—Design and Initial Evaluation", IEEE Transactions on Medical Imaging, vol. 21, No. 8: 991-997 (2002).
Office Action for European Patent Application No. 13785660.5, dated Jan. 18, 2019.

* cited by examiner

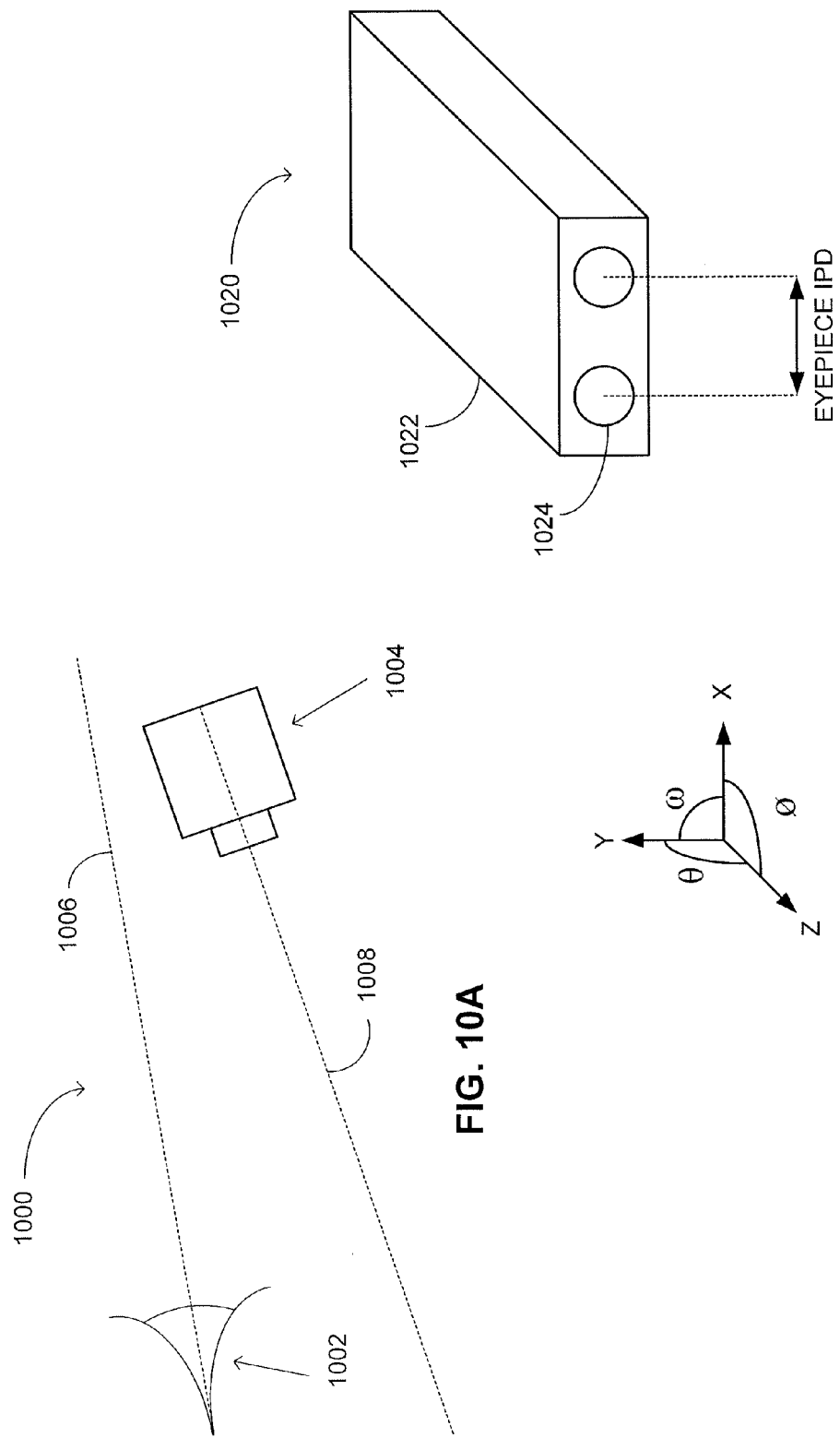

MICROSURGERY SYSTEM FOR DISPLAYING IN REAL TIME MAGNIFIED DIGITAL IMAGE SEQUENCES OF AN OPERATED AREA

This application is a Continuation-in-Part of PCT/IL2013/050764, filed 10 Sep. 2013, which claims benefit of Serial No. 221863, filed 10 Sep. 2012 in Israel and which applications are incorporated herein by reference. To the extent appropriate, a claim of priority is made to each of the above disclosed applications.

FIELD OF THE DISCLOSED TECHNIQUE

The disclosed technique relates to microsurgery, in general, and to systems and methods for displaying in real-time magnified digital image sequences of an operated area for allowing a user to perform procedures in the operating room, or microsurgery in particular.

BACKGROUND OF THE DISCLOSED TECHNIQUE

Microsurgery is a general term for surgical procedures utilizing a surgical microscope to perform intricate operations on small structures. Through the microscope the surgeons sees magnified imaged of the structures or tissues. Currently microsurgery procedures utilize a classic conventional optical microscope. The basic conventional surgical microscope is constructed of high quality optical components, zoom objective lens, eyepiece for user view, light source and an XY motor. Microscopes usually have provision to have additional eyepieces for assistance. For some procedures, like neurosurgery, the microscope is connected to complex motion structures, providing motion in even 6 degree's in space. In addition, there are some more add-ons for special functions like cameras to capture/record the operation, projection displays to project symbols, UV light sources etc. The common ground for surgical microscopes is the stereo image, their fixed position above the patient (around 20-40 cm) and the connection of the user (or surgeon) to the microscope which sees the relevant object through direct optical channels. There are techniques to fold the light rays in the microscope to design a more comfortable and ergonomic structure for the user. However, because the microscopes are based on direct light rays channels, they are limited in their ability and flexibility to locate and shift the eyepiece. Simply put, the eyepiece of the conventional surgical microscope is mechanically connected to the optical system of the microscope, making the surgeon connected the microscope as well. During prolonged use of the microscope (in particular, surgical operations), the user must position her head fixed to the microscope for a long period of time. The long time that the user holds her head fixed to the microscope causes neck/back pains, fatigue and may influence the procedure quality.

Conventional microscopes are bulky and big, located in the most sensitive areas in the operation room, above the patient. The microscopes may obstruct the view and the motion of the medical staff around the operated area. When more than a single surgeon uses the conventional surgical microscope, all surgeons are constrained to view the same image with the same magnification. If the additional surgeon would have wishes to view a different field or a portion of the same field but at a different magnification, an additional microscope would have been required, thus further encumbering the operating room. Further additionally, due to the classic direct view method of the microscope, with no digital means and sensors, the users do not benefit the digital domain advantages.

Reference is now made to US Patent Application Publication No. 2009/0245600, to Hoffman et al., and entitled "Automated Panning and Digital Zooming for Robotic Surgical Systems". This publication describes an endoscopic system for minimally invasive procedures. The endoscopic system acquires endoscopic images at a slightly higher resolution than that of the display, thereby allowing for digital zoom or panning. That is, the system selects a region of interest (ROI) for displaying to the user and crops the ROI out of the acquired image to fit into the display. The user views the cropped ROI via dedicated eyepieces or monitor, and therefore cannot move freely around the operating room while viewing the ROI. This publication describes employing robotic arms for performing surgical operations. The robotic arms obstruct the operating area. For example, the robotic arms might occlude a portion of the operating area and might obstruct the surgeon's access to the operating area. The camera in this publication is an endoscopic camera fitted into an endoscope and is therefore limited in size and resolution.

Reference is now made to International Patent Application Publication No. WO2011/142165, to Ogawa, and entitled "Operation Input Device and Manipulator System". This publication describes an operation input device for employing robotic arms for performing remote surgeries. The operation input device includes a display, an operation unit, a head-mounted unit, relative position sensors, and a control unit. The operation unit operates a displayed object (e.g., a surgical robotic arm), which is displayed upon the display. The relative position sensors detect the relative position and the relative orientation of the head-mounted unit with respect to the operation unit. The control unit actuates the displayed object which is displayed within the display on the basis of the relative position and the relative orientation that have been detected by the relative position sensors.

SUMMARY OF THE DISCLOSED TECHNIQUE

It is an object of the disclosed technique to provide a novel method and system for displaying in real time magnified digital image sequences of an operated area, which overcomes the disadvantages of the prior art. In accordance with the disclosed technique there is thus provided a microsurgery system including a Head Mounted Display (HMD), at least one camera, a memory unit and a processing device. The processing device is coupled with the HMD, the camera and with the memory unit. The camera is suspended above an operated area, and acquires operated area image sequences of the operated area. The memory unit stores the operated area image sequences. The processing device receives an input indicating a Region of Interest (ROI) of the operated area. The size of the operated area is larger than the size of the ROI. The processing device produces magnified image sequences of the ROI from the operated area image sequences. The HMD displays to a user in real time the magnified image sequences of the ROI. The camera is mechanically and optically disconnected from the HMD.

In accordance with another embodiment of the disclosed technique, there is thus provided a method for displaying in real time magnified digital image sequences of an operated area. The method includes the steps of acquiring operated area image sequences, receiving an input indicating a Region of Interest (ROI); producing magnified image sequences of the ROI and displaying in real time the magnified image sequences of the ROI. The operated area image sequences are acquired from a viewpoint suspended above the operated area. The size of the operated area is larger than a size of the ROI. The magnified image sequences of the ROI are produced from the operated area image sequences. The magnified image sequences of the ROI are displayed to a Line of Sight (LOS) of a user, which is independent of the viewpoint of the operated area image sequences.

BRIEF DESCRIPTION OF THE DRAWINGS

For better understanding of embodiments of the invention and to show how the same may be carried into effect, reference will now be made, purely by way of example, to the accompanying drawings in which like numerals designate corresponding elements or sections throughout. In the accompanying drawings:

FIGS. 10A and 10B are schematic illustrations of a display system having adjustable eyepieces, constructed and operative in accordance with yet a further embodiment of the disclosed technique.

DETAILED DESCRIPTION OF THE EMBODIMENTS

1 Basic System

Figure 1:
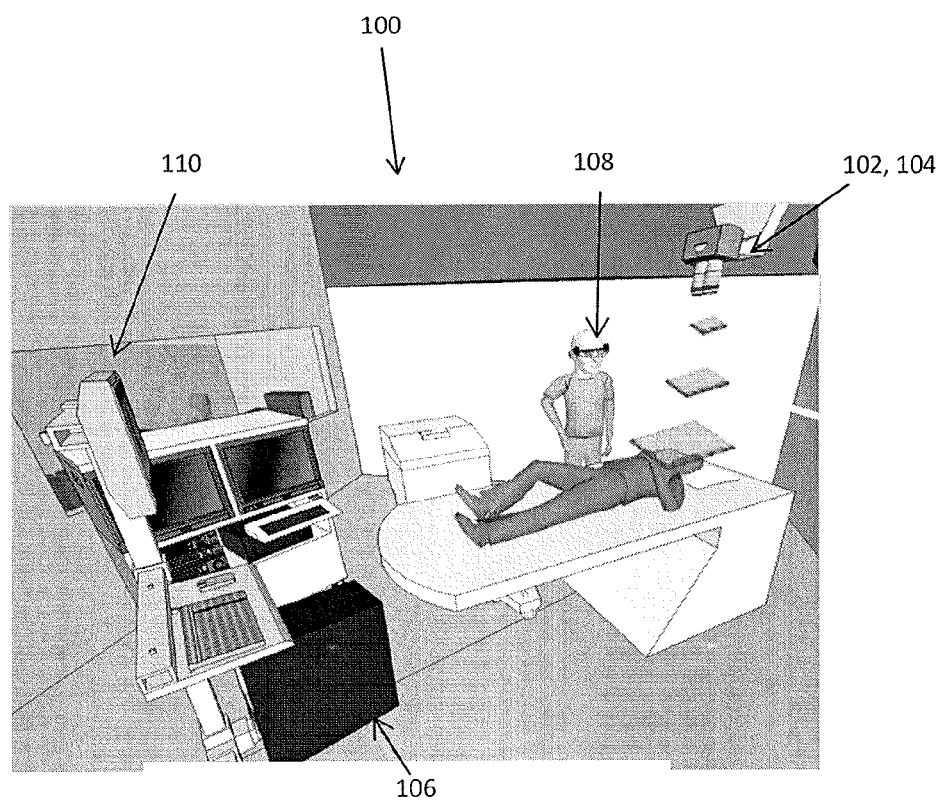
FIG. 1 is a schematic illustration of a microsurgery system for displaying in real-time ROI image sequences of an ROI of an operated area, constructed and operative in accordance with an embodiment of the disclosed technique.

Before expansion of the drawing details, the following paragraphs briefly describe some aspects and building blocks of the systems of the disclosed technique. The disclosed technique relates to a microsurgery systems designed to replace a conventional surgical microscope in the operating room (OR). The microsurgery system of the disclosed technique includes digital cameras suspended above the operated area, Head Mounted Display (HMD) and a processor. Additionally a light source and monitor are usually integrated with the system. The cameras can be mounted on a support arm (e.g., attached to the ceiling, the wall or supported on a pole). The cameras and HMD are used to display to a user, in real-time, live video (image sequences) of an operated area, allowing the user to perform microsurgical procedures. While using the disclosed technique, the user performs microsurgery procedure without employing a conventional surgical microscope, which can be removed from the OR altogether.

The processor captures the data from the cameras, processes it and transmits it to the HMD's and monitors. Each user can control the data and processing functions made for his display or use. The cameras and the HMD are not mechanically connected (i.e., are mechanically disconnected), and are optically disconnected. Thereby, the user's head position is not limited or constrained, by the position of the surgical microscope (like conventional microscopes constraining the position of the eyepieces). Additionally the cameras are suspended above the operated area, and therefore do not obstruct the operated area (i.e., do not occlude the operated area and do not physical obstruct the user's access to the operated area). That is, removing the surgical microscope from the OR and replacing it with cameras suspended above the operated area frees the OR from the physical obstruction caused by the conventional surgical microscope. Thereby, the user is provided with more freedom to move around the OR, and in particular around the operated area (i.e., also referred to as the target area).

In accordance with one embodiment of the disclosed technique, the system includes at least two high resolution video cameras suspended above the operated area, a processing device and an HMD. The cameras capture image sequences of the operated area (i.e., operated-area image sequences) from at least two slightly different perspectives. The processing device receives the operated-area image sequences and produces therefrom stereoscopic, or three dimensional (3D), image sequences of the operated area. The processing device presents the image sequences to the user via an HMD in real-time. The user performs microsurgery procedures based on to the 3D image sequences.

The image resolution of the cameras is much higher than that of the display components of the HMD, such that for small magnifications, the acquired operated-area image sequences must be downscaled or resized to fit into the display. For example, for displaying an area smaller than the full image frame, the processing device determines an ROI within the acquired operated-area image sequences. The processing device crops ROI image sequences from the acquired operated-area sequences, resizes it to fit the display resolution, and displays the ROI to the user via the HMD. The term ROI image sequences, as referred to herein below, refers to the cropped ROI portion cropped from the acquired operated-area image sequences. The term ROI image sequences may further relate to (i.e., the ROI image sequences may further include) metadata relating to the viewing angle, type of objects to be viewed, and further data that may be presented within the ROI image sequences such as messages and alerts.

HMD 208 is a dual-eye display. Employing HMD 208 detaches the user from a monitor or eyepieces and enables her to move freely around the OR. Additionally, the ROI can be slaved to HMD 208 (i.e., as tracked by tracker 218) thereby conveniently providing the user with the ROI image sequences she is interested in. HMD 208 can allow 2D or 3D view, according to the nature of the application and video source. HMD 208 may include display optics in front of one, or of each eye.

Angular resolution is the angle of the smallest apparent object noticeable in the electro optical system. The angular resolution of an image forming device, describes its ability to distinguish small details of a scene at a selected distance. In a camera, the angular resolution will be referred as Instantaneous Field of View (IFOV), and is given by the pixel size divided by the effective focal length of the optics (e.g., measured in radians). Thus, the IFOV of the camera is a property of the pixel and of the optical system, and is not related to the number of pixels in the image sensor. For a given IFOV, the number of pixels of the camera sensor (i.e., the pixel count) defines the Field of View (FOV); or together with the distance to the object, defines the size of the captured area. The cameras of the microsurgery system of the disclosed technique have IFOV that is small enough to resolve details of micrometric dimensions (e.g., five microns) in the operated area, from the position of the cameras suspended above the operated area. It is noted that in a monitor display, the IFOV is the smallest projection element divided by the distance to the viewer. In an HMD the IFOV is the smallest projection element divided by HMD focal length.

The HMD of the microsurgery system of the disclosed technique has an IFOV close to the human eye limit, achieved by the ratio between the pixel size and the effective focal length. That is, the HMD allows the user to view the displayed image sequences at the highest acuity (i.e., lowest IFOV) the user eye is capable of. The IFOV of the HMD, together with the display resolution of the HMD, provide the required HMD FOV at the desired acuity to allow the user to perform a microsurgical procedure.

The magnification of a system with a camera and a display is proportional to their ratio. The IFOV of the cameras and distance from object sets the smallest visible object that can be digitally captured. The pixel count of the cameras sets the area covered by the camera. The ratio between the display IFOV and the camera IFOV sets the maximum magnification in such a manner (e.g., for observer located 40 centimeters (cm) from the object):

$$\text{Maximum Magnification} \approx \frac{40\text{ cm} \cdot IFOV_{HMD}}{\text{Camera Distance} \cdot IFOV_{camera}}$$

To achieve a large range of magnifications, the camera pixel count must be larger than of the pixel count of the display. Pixel count describes the number of pixels of a camera sensor or of a display. For example, if the HMD has IFOV close to the human high, around 0.0003 radians and the camera IFOV is 0.00001 radians the maximum magnification, for a camera distance of 40 cm is 30. If the HMD resolution is 1920×1200, than to create a range of magnifications between 10 and 30, the camera resolution should be at least 5760×3600 pixels. That is to cover the full HMD display area with the entire range of magnifications.

The microsurgery system of the disclosed technique can provide digital object magnification at least comparable with that of conventional surgical microscopes. Digital image magnification eliminates the need (or at least compliments) for optical zoom mechanism. Thus, the microsurgery system of the disclosed technique can operate without an optical zoom mechanism, thereby saving the space and the costs thereof. Additionally, changing the optical zoom requires mechanical movement of lenses which might take more time than digital magnification via image processing, and is more prone to wear and tear. Further additionally, the digital images and digital image magnification allows for further advantages associated with the digital domain, such as fast movements between ROIs. That is, the system can switch an image of a first ROI with an image of a second ROI between frames.

The microsurgery system of the disclosed technique images a large operated area at all-times, and thereby can improve the situational awareness of the user and can be used for additional applications. That is, in a conventional surgical microscope of the prior art, the observed (i.e., and magnified) FOV is narrow and gets even narrower with magnification. The user of the conventional surgical microscope might miss important visual cues outside the observed field. The microsurgery system of the disclosed technique captures visual data from a large area, even if the user is currently interested (i.e., magnifies and observes) a narrower ROI. Thereby, the microsurgery system can provide data respective of the area surrounding the ROI, which may be pertinent to the surgery or can be used for situation awareness, fast jump between areas, image processing and tracking, etc.

The microsurgery system displays the full operated-area image sequences, or the magnified ROI image sequences, in real-time such that the user can perform a microsurgical procedure in real-time, accordingly. Therefore, the time lag from the acquirement of the operated-area image sequences to the display of those images, or of the ROI image sequences should be very brief. Delays can impact performance of operation and can create discomfort, fatigue, and the like, to the user. The term "real-time" as referred to herein below relates to an instantaneous action, or a very short time lag, allowing for smooth operation of the user. That is, the user should not experience noticeable time lag between an event occurring on the object plane and the display of that event. Short latency can be achieved using fast read out cameras, powerful processors and efficient logic and algorithms implemented in the processors. In some embodiments the latency can be decreased by grabbing and processing only the regions of interest and, thereby decreasing the required data band width.

Reference is now made to FIG. 1, which is a schematic illustration of a microsurgery system, generally referenced 100, for displaying in real-time image sequences of an operated area, constructed and operative in accordance with an embodiment of the disclosed technique. With reference to FIG. 1, microsurgery system 100 includes a pair of cameras 102 and 104, a processing device 106 and a Three Dimensional (3D) HMD 108. Processing device 106 is coupled with each of cameras 102 and 104, and with HMD 108. Microsurgery system 100 is installed within an OR (not referenced) and replaces a conventional surgical microscope. That is, microsurgery system 100 allows the user to perform microsurgeries by presenting to the user image sequences of the operated area (not referenced) in real-time, and at a desired magnification.

As can be seen in FIG. 1, cameras 102 and 104 are suspended above the operated area. Cameras 102 and 104 do not obstruct the user from accessing the operated area. Cameras 102 and 104 are mechanically (and optically) disconnected from HMD 108. The captured image sequences are displayed via HMD 108. Thus, the user is not constrained to an eyepiece or a monitor and is free to move around the operating room.

In a nutshell, microsurgery system 100 operates in the following manner. Cameras 102 and 104 capture image sequences of the operated area (i.e., also referred to as operated-area sequences). Processing device 106 determines a Region of Interest (ROI) of the operated area. For the general purpose from here on, ROI can also be considered as the full operated-area frame. Processing device 106 produces ROI image sequences from the acquired operated-area sequences and presents the ROI sequences to the user via HMD 108. The pixel count of cameras 102 and 104 is higher than that of HMD 108, and therefore the operated-area sequences should be resized (i.e., downsized) for fitting into the display. Additionally, in case the ROI is only a portion of the operated area, processing device 106 crops the respective portion from the operated-area sequences for producing the ROI sequences. For example, assuming the user wishes to view a selected section of the operated area, processing device 106 would crop the portions of the operated-area sequences showing that selected section, and would downsize the cropped portions for producing the ROI sequences. The ROI size and the resizing value, along with the camera distance from the object, will determine the magnification.

Processing device 106 can further perform additional image processing operations on the captured sequences. Moreover, processing device 106 can further present to the user additional data (e.g., medical history; physiological measures; and medical imaging data, such as CT or MRI) overlaid on the captured sequences. As mentioned above, the displayed ROI sequences can further include metadata relating to magnification, illumination levels, data on of objects to be viewed, symbolics, guidance and data that may be presented within the ROI sequences such as messages and alerts.

Figure 2:
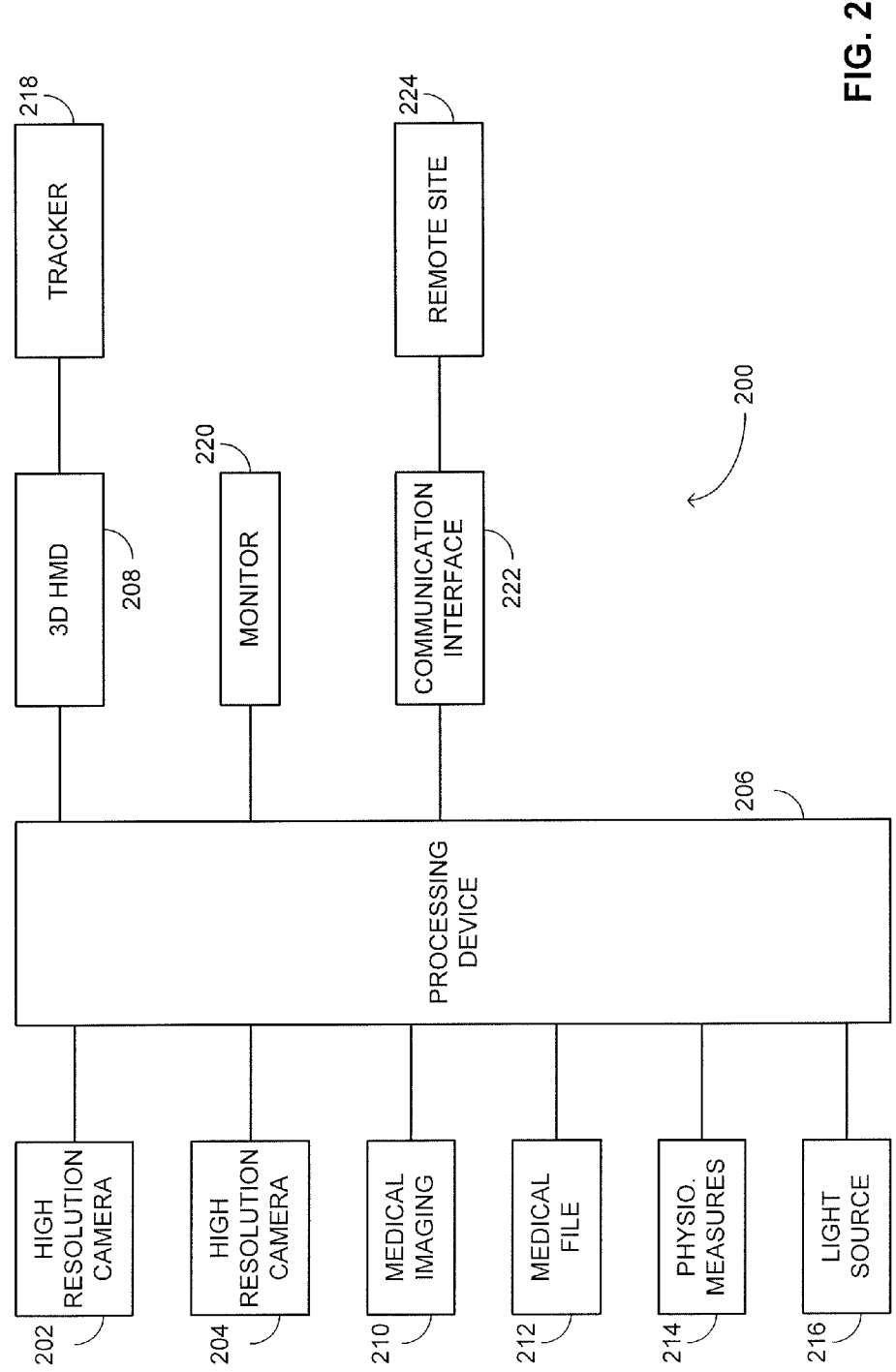
FIG. 2 is a schematic illustration of a block diagram of a microsurgery system for displaying in real-time ROI image sequences of an ROI of an operated area, constructed and operative in accordance with another embodiment of the disclosed technique.

Reference is now made to FIG. 2, which is a schematic illustration of a block diagram of a microsurgery system, generally referenced 200, for displaying in real-time ROI image sequences of an ROI of an operated area, constructed and operative in accordance with another embodiment of the disclosed technique. Microsurgery system 200 includes a pair of cameras 202 and 204, a processing device 206, a 3D HMD 208 having a tracker 218 (e.g., a head tracker or/and an eye tracker), a medical imaging image source 210, a medical file data source 212, a physiological measures source 214, a light source 216, a monitor 220, a communication interface 222 and a remote data site 224. Microsurgery system 200 can further include user interfaces, such as joysticks, keyboards, levers, buttons, pedals to be used by the user using her feet, and the like. Processing device 206 is coupled with each of the pair of cameras 202 and 204, 3D HMD 208, tracker 218, medical imaging image source 210, medical file data source 212, physiological measures source 214, light source 216, monitor 220, and with a remote data site 224 (i.e., via communication interface 222). Processing device 206 includes, or is coupled with, a memory unit (not shown) for storing data thereon.

The following paragraphs provide a general description of the operation of microsurgery system 200. Thereafter, each of the components of the microsurgery system would be described more elaborately, followed by some additional functionalities and embodiments of the system. During operation, cameras 202 and 204 capture video sequences of the operated area (i.e., operated-area sequences). Processing device 206 receives input indicating an ROI (e.g., indicating the location and size of the ROI) in the operated area, and accordingly produces respective ROI sequences from the acquired operated-area sequences (i.e., by resizing and possibly cropping). That is, processing device 206 crops a portion of the captured operated-area sequences according to the determined ROI (i.e., crops the respective portion of the acquired sequences showing the ROI), and resizes the cropped sequences for producing ROI image sequences. Processing device 206 displays the ROI sequences to the surgeon via HMD 208.

For example, processing device receives input detailing the Line of Site (LOS) of the head or of the eye of the user from tracker 218. Processing device 206 determines the ROI according to the tracked LOS. The ROI can be also extracted from user input received via a joystick, a keyboard, a foot pedestal, voice activation, and any other input device. According to another embodiment of the disclosed technique, the ROI is derived by tracking a point of a tool (e.g., a scalpel) held by the surgeon or other features in the image. In this case the ROI can be updated in real-time as the operation progresses.

Microsurgery system 200 allows zooming in to the image digitally, providing digital XY translation motion of the image, and simultaneously providing different users with different ROI image sequences. By capturing the full camera resolution at all-times, microsurgery system 200 can perform the following, exemplary, functions:

Record the entire FOV of the cameras for debriefing and later analysis.

Share the image observed by the user for the purpose of teaching or receiving assistance.

Serve multiple users, including staff or processors.

Keep track of features not currently observed by the surgeon and out of his current field of view.

Save bookmarking of areas or other ROI's in the image.

The following paragraphs elaborately describe the various components of microsurgery system 200. As mentioned above, cameras 202 and 204 replace the conventional surgical microscope, which can therefore be removed from the operating room completely. By replacing the conventional surgical microscope, and enabling removal thereof from the operating room, the microsurgery system of the disclosed technique removes an obstruction from the operated area. Thereby, a better view and more space are available to the medical staff around the operated area. Each of cameras 202 and 204 can includes optical elements, such as lenses (e.g., objective lenses or field lenses), prisms, and every other optical component required for acquiring high resolution, large FOV images.

Cameras 202 and 204 can either be fixed in place or moveable by a dedicated mechanism. Cameras 202 and 204 are suspended above the operated area. Cameras 202 and 204 can be suspended from the ceiling, a wall or from a support frame (e.g., a support frame mounted on the floor or a suspended support arm). In this manner, cameras 202 and 204 do not obstruct the operated area (i.e., do not occlude the operated area to any of the users, and do not physically obstruct access to the operated area). In accordance with another embodiment of the disclosed technique, cameras 202 and 204 have objective lenses capable of focusing on objects at a distance of tens of Centimeters, for example, 15-150 Centimeters. Thereby, cameras 202 and 204 can be suspended above the operated area, and capture the image sequences of the operated area from a far.

Cameras 202 and 204 capture operated-area image sequences from two different perspectives to be displayed to each eye, providing 3D imaging. It is noted that the relative position of the cameras, from each other, can also be varied, for example, according to the distance from the object. Alternatively, more cameras can be employed for capturing operated-area sequences from various perspectives. For example, microsurgery system 200 can include three, four, or six cameras. In this manner, the 3D captured data is enriched, and occlusions to a selected camera can be compensated for. Further alternatively, a single camera is employed for capturing images from different angles by utilizing a special optical assembly or an actuating assembly.

Processing device 206 controls cameras 202 and 204, and can control Automatic Gain Control (AGC), Exposure Control (EC), Iris Control and any other control method for setting the cameras working point. In addition processing device 206 can set the frame rate of cameras 202 and 204.

Light source 216 is arranged to illuminate the operated area. For example, light source 216 can be arranged to illuminate the operated area from the cameras optical LOS creating a coaxial or semi coaxial illumination. In some applications the light source can produce collimated illumination. Another approach is to illuminate from a singular point at some location near the lens creating a flood light. A third approach may be to use more than a single light source. For instance, the multiple sources can be the ones described in the first two approaches. Alternatively, a ring of light sources can be designed around the lens. The distribution of light sources can be arranged to produce uniform light with less shadowing in the image.

Additionally, one or more of light sources 216 can illuminate in the Near-Infrared (NIR) spectrum, UV or any other light spectrums for capturing video sequences at the respective spectrums, or for exciting a fluorescent agent. The different illumination spectrums can be produced by different light sources, or by employing different filters. Instead of designing the light sources for different spectrums, or in addition, the camera can be designed to capture images in different spectral bands.

Processing device 206 can be replaced by another processing device or an array of processing devices, and can have either a centralized or a decentralized configuration. The memory unit can be replaced by, or augmented with, other data storage devices.

Monitor 220 can display the acquired image sequences, or cropped and resized portions thereof. Thereby, all personal within the OR (and not only those equipped with an HMD) can view the acquired sequences. Alternatively, processing device 206 employs monitor 220 for displaying additional data, such as the medical history of the patient.

Medical imaging image source 210, medical file data source 212, and physiological measures source 214 are all data sources for providing external data, which can be displayed to the user besides the ROI image sequences. These data sources would be detailed further herein below with reference to section 6.

Tracker 218 can be a head tracker, an eye tracker, or both, for tracking the position and orientation, or at least the Line of Sight (LOS) of the user. Tracker 218 can be an optical tracker, a magnetic tracker, an ultrasonic tracker, or any other tracker, and would be detailed further herein below with reference to section 4.

Communication interface 222 enables microsurgery system 200 to communicate with a remote data site 224, for example for providing image sequences of the operated area to remote data site 224, or to receive data from remote data site 224. For instance, microsurgery system can provide ROI image sequences to a surgeon located on a remote site, in case the user wishes to consult with that surgeon. Communication interface 222 would be detailed further herein below with reference to section 5.

It is noted that out of the components of microsurgery system 200 detailed herein above, only the cameras, the processing device and the HMD are compulsory—everything else is optional and various combinations can be constructed (or employed) for various tasks, procedures, and resource constraints.

2 System Features

Other functionalities and structures of microsurgery system 200 are described herein. The optics (not shown) of cameras 202 and 204 can provide further magnification (i.e., optical magnification). In this manner, the cameras do not provide unmagnified images, and the magnification range of microsurgery system 200 begins at the optical magnification factor and extends by digital magnification. For example, if optical design of the cameras produces optical magnification of a factor of four (×4) and the digital magnification can be up to ×6, the magnification range would be ×4-×24. Put another way, the cameras capture images at a constant optical magnification, and can further provide digital magnification due to their high resolution design.

As mentioned above, cameras 202 and 204 provide the captured operated-area sequences to processing device 206. Processing device 206 crops and resizes the image sequences for producing ROI image sequences and provides the ROI sequences to HMD 208 for displaying to the user. Microsurgery 200 captures a wide FOV images. The objective optics of the cameras produce (i.e., focus) an image of the operated area to be captured by the cameras (i.e., by the sensors of the cameras). In accordance with one embodiment of the disclosed technique, the cameras capture wide FOV images covering the image of the operated area as focused by the objective optics of the cameras. After determining the ROI, processing device 206 produces ROI image sequences from the captured operated-area sequences by cropping a respective portion of the captured operated-area sequences (and resizing it).

In accordance with another embodiment of the disclosed technique, the camera IFOV is the same as in the previous embodiment but the FOV of the camera is smaller (smaller sensor resolution). In this case, the cameras are capable of mechanical motions, like XY movement or optical zoom, to capture FOV extending beyond the camera FOV (i.e., to be able to capture every location of the FOV of the objective optics). The camera captures a portion of the FOV of the objective optics respective of the determined ROI, thereby decreasing the amount of data to be handled by the system, while still maintaining the necessary IFOV. For instance, the LOS of the camera can be enslaved to a head tracker, or to an eye tracker (or to another user interface, such as joysticks), for capturing ROI image sequences. It is noted that the captured ROI image sequences might still require resizing to fit the display, depending on the pixel count of the camera and that of the display. The XY motion mechanism can be implemented by a bi-axial steering mirror that scans the image obtained by the objective optics through a wide FOV. The position and/or orientation of the mirror is enslaved to the user's head (or eye) movements (or controlled by another user interface), replacing the cropped area of the solution mentioned in the previous paragraphs. Another method for shifting the LOS of the camera is using pan and tilt mechanism of some elements of the system.

In accordance with yet another embodiment, there is a combination of the two previously described embodiments (i.e., the embodiments of the wide FOV camera sensor that captures the entire FOV of the objective optics and of the narrower FOV camera sensor with the scanning mechanism). In the combined embodiment, the camera sensor has a moderate FOV and is complimented by scanning possibilities. In addition a selected ROI image sequence is cropped and resized for displaying to the user.

As mentioned above, processing device 206 receives the operated-area image sequences acquired by cameras 202 and 204, and receives input indicating an ROI of the operated area (e.g., the LOS of HMD 208 determined by tracker 218 or from the joysticks movements). Processing device 206 crops and resizes the acquired image sequences for producing ROI sequences. The cropping of the ROI sequences out of the full frame can be carried out in several methods. The first method involves grabbing the full image out of the sensors of cameras 202 and 204. In this method the ROI portion is digitally cropped from the full image after the grabbing. The second method involves grabbing only the ROI portion from the sensors of cameras 202 and 204 (and not the full frame). The grabbing can be made by addressing only the relevant pixels in the image array. In the first two methods, processing device 206 performs image resize on the cropped ROI portion so it will fit the resolution of HMD 208. In case the ROI covers the entire captured field, so that no cropping is required, the digital image sensors of cameras 202 and 204 can be configured to under-sample for adjusting the pixel count of the video sequence to the pixel count of HMD 208. An example of under-sampling is the sampling of every second pixel in the array instead of every pixel.

In accordance with another embodiment of the disclosed technique, light source 216 can provide visual guidance to the user. For example, if the light is in the visible spectrum, it can be used to mark areas of interest, mark places to perform surgery cuts, direction symbol, and the like. Illuminating in the near-infrared can be used for structured light applications. The structured light is used to produce 3D data base of the objects. The projector can be of any type, such as Digital Micromirror Device (DMD), Pico Micro-electromechanical Systems (MEMS) projector, Liquid Crystal Display (LCD), Cathode Ray Tube (CRT), and the like.

Cameras 202 and 204, and light source 216 can be digitally controlled. For example, system 200 can employ algorithms like AGC and AEC to calculate and set the camera working point. The gain and exposure are usually calculated to produce image with maximum dynamic range and minimum saturations. With a single or multiple light sources an Automatic Light Control (ALC) may be used. Based on the image the algorithm calculates the light levels of the single or multiple light sources. The controllable light sources facing the scenes are dynamically adjusted based on a dynamic analysis of the image histogram of the video sequences. The level of the lights are adjusted to optimize the contrasts, dynamic range and to minimize specular reflections from objects.

Alternatively the light source can be time modulated. In this case the source transmits pulses of light in some kind of time scheme (Meaning, the light source is turned on and off multiple times per second or minute) and the cameras are synchronized to the light source time regime. This synchronization of the cameras and the light source can be used for some features of the microsurgery system, exemplary ones are detailed in the following paragraphs. For example, if the integration time of the camera is lower than the cameras frame time (inverse of the camera refresh rate) the light source on time can be reduced to overlap with the camera integration time. Illumination power is saved in this case. Another example is time of flight technique or gated imaging. That is, the source is configured to transmit a very narrow pulse (with time) of light. The camera is synchronized to open its shutter only after the time of which the pulse has traveled to the object and came back. This technique can be used with one pulse per frame or with multiple frames per frame to increase the signal received by the camera. By known and correct synchronization of the camera and light source, using this method can help to create a 3D data base of the object or even to penetrate the tissues.

Alternatively the light source can be designed to illuminate the operated area with different intensities. For instance, the operated area is divided into sub areas smaller than the operated area. Each area is illuminated with different intensity to increase to dynamic range of the image and illuminate saturations, dazzling, dark spots and so on. In the simplified manner each sub area can be illuminated using different light source. Each light source is controlled separately to derive its individual illumination value. A more efficient manner is a light source designed with array of switching shutters. The light source illuminator is composed of a source (e.g., LED, Xenon, Laser, Halogen, Fiber, etc.) and an optical module designed to illuminate the operated area with the source. The optical module is usually designed to transmit in a relatively narrow angle and to create a uniform illumination spot on the operated area. The shutter array is implemented inside the optical module in a location where the beam is collimated, semi collimated, in an aperture stop, field stop or in a focal plane. In this way each shutter controls the illumination level correlated to a specific directional illumination of the operated area.

The shutter arrays can be transmitting shutters like LCD array, or reflective shutters like digital micro mirror device (DMD). For the purpose of the following description we will use the DMD as the shutter array. The light source illuminates in a relatively large angle and non-uniform pattern. A set of first lenses can be used to collect the light rays from the source to the shutter array. As an example, the first lenses focus the light beam to the shutter array. When the all the mirrors of the array are in the ON position the set of second lenses collimates the image created on the shutter array to the operated area. The image created on the shutter area falls and multiple small shutters (in the case of DMD, can reach millions of micro mirrors). Reflection from each mirror on the area corresponds to a small area on the operated area. For a specific mirror, if it is OFF position, the small area corresponding to that specific mirror will not be illuminated. If the shutter area is operating in higher rate than the frame rate of the camera, then the small area can be partly illuminated by controlling each micro mirror frequency per camera frame.

The processor controls the value of each of the shutter in the shutter array. They can be configured in advance or can be dynamically changed according to the image for example. If the processor identifies that an area in the image is saturated it can decrease the illumination level from the corresponding shutters. Separately, or together with the camera gain and exposure control, this can increase significantly the dynamic range of the image.

Alternatively, the camera sensor can be gated. In this manner, each of the camera pixels can be configured individually for its triggering. The configuration can incorporate the number of ON and OFF exposure opening per frame (multiple pulses per frame) and can incorporate the time duration of the on time and off time (pulse widths). By controlling the exposure time of each pixel the dynamic range of the image can be increased.

2.1 Voice Activation

Microsurgery System 200 can further include a voice control module allowing control of system 200 via voice activation. Voice activation allows hands-free control, leaving the user's hands free to perform any task, while providing a flexible and a rich control interface. The voice control module allows the identification of pre-programmed keywords, reserved for specific purposes, to be used by any user, and to allow users to program their own keywords, independent of a language or dictionary. For example, the oral command "markers on" may add pre-defined markers onto the displayed image. The voice control module can be programmed to include any command required for a specific user.

The voice control can be programmed to be adapted to users speaking different languages. For example, a Spanish-speaking user may supplement the English commands with its native language commands by programming the Spanish commands herself.

Voice activation can be used in conjunction with the head and eye trackers to construct elaborate yet intuitive user interface. For example, a "zoom on" oral command may toggle on a head-movement-dependent zoom function. For instance, moving the head forward zooms into the image, while moving it backwards zooms out. A "zoom off" command toggles this feature off, allowing for normal operation.

2.2 Gestured Control

In accordance with another embodiment of the disclosed technique, microsurgery system 200 can further include a gesture control module allowing control of system 200 via gestures. That is, the head tracker or eye tracker of the microsurgery system captures the head or eye movements of the user. The processing device interprets predefined gestures, and accordingly operates respective functions of the microsurgery system. For example, the user can move her head forward to activate a "zoom in" function, or move her head away to activate a "zoom out" function (the same can be for focus instead of zoom). Another example can be shifting between screens displayed on the HMD. Fast head movement (or other defined movement pattern) to the left/right/top/bottom (or any other direction) toggles between different screens or image source inputs (or in the general manner different configurations). The gesture control module can be activates and deactivates by a predefined gesture (or a voice command or a button), to avoid movements from being interpreted as unintentional gestures.

More specifically, the head movements can be used in a virtual menu seen on the HMD. The user activates the virtual menu by a predefined gesture (or a voice command or a button). Once the virtual menu is operated the user can activate the functions of the virtual menu be moving the head or eyes to that specific button or function.

2.3 Stereo Imaging

Figure 3:
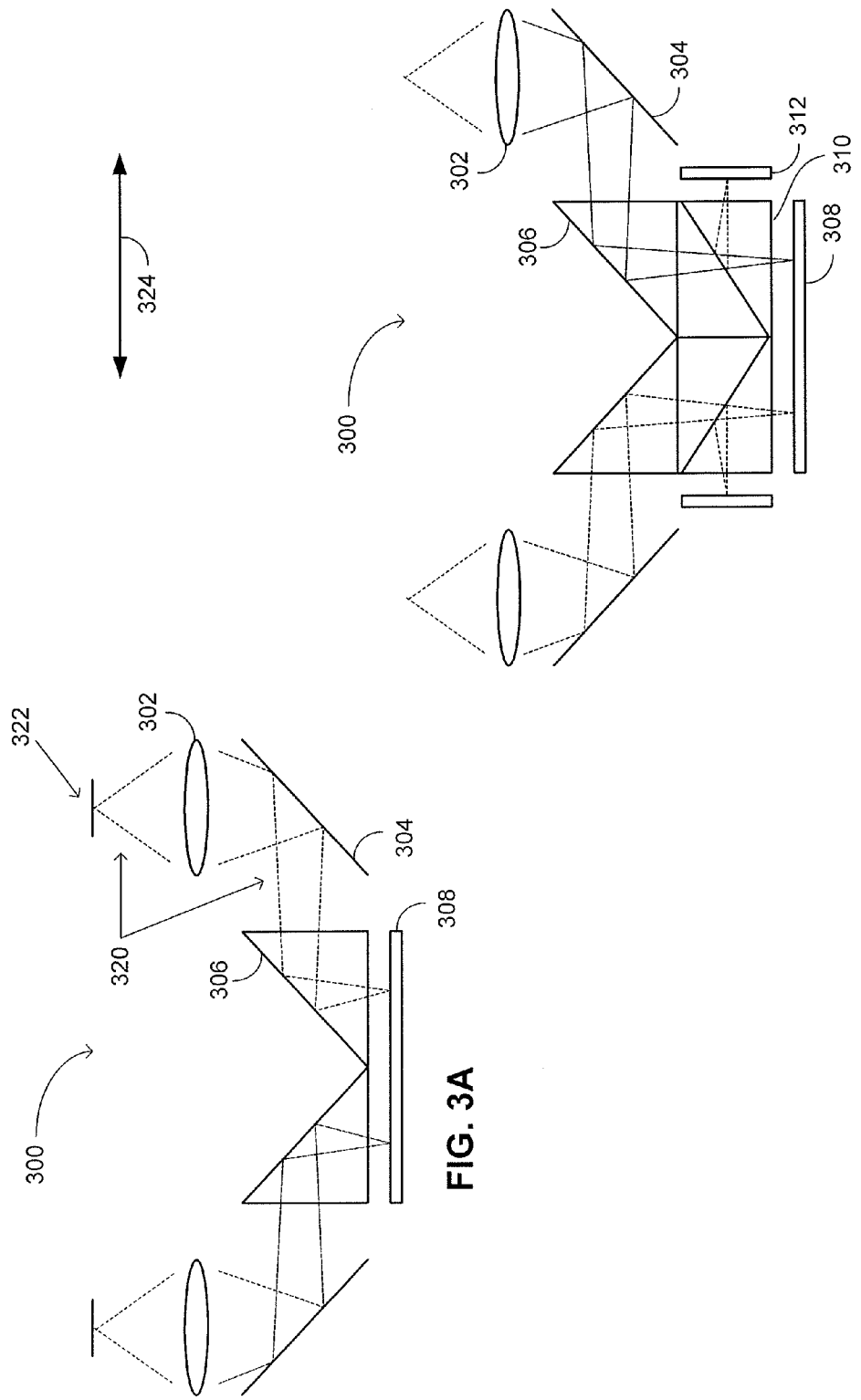
FIGS. 3A and 3B are schematic illustrations of a stereoscopic optical system for acquiring a stereoscopic image pair by employing a single sensor, constructed and operative in accordance with a further embodiment of the disclosed technique.

Reference is now made to FIGS. 3A and 3B, which are schematic illustrations of a stereoscopic optical system, generally referenced 300, for acquiring a stereoscopic image pair by employing a single sensor, constructed and operative in accordance with a further embodiment of the disclosed technique. FIG. 3A depicts a stereoscopic system including two optical systems and a single image sensor. FIG. 3B depicts a stereoscopic system further including an infrared sensor complimenting each of the optical systems. Stereoscopic optical system 300 can be incorporated into the microsurgery system of the disclosed technique for acquiring stereoscopic images of the operated area with a single ultrahigh resolution sensor, replacing both cameras (e.g., replacing cameras 102 and 104 of FIG. 1, or cameras 202 and 204 of FIG. 2).

In FIGS. 3A and 3B only one side of stereoscopic system 300 is enumerated, though the description applies to both sides. With reference to FIG. 3A, stereoscopic system 300 includes an optical relay system 302, a dynamic mirror 304, a fixed mirror 306, and an image sensor 308. Optical relay system 302 is optically coupled with dynamic mirror 304, which in turn is optically coupled with fixed mirror 306. Fixed mirror 306 is further optically coupled with image sensor 308. In particular, the numerally indicated elements in FIG. 3A composing the right side optical path of stereoscopic system 300, and constituting a right optical system, direct a right side image onto the right side of sensor 308. Similarly, the left optical system of stereoscopic system 300 (not numerally indicated) direct a left side image onto the left side of sensor 308 via a left optical path.

Optical relay system 302 is an optical system for relaying an intermediate image 320 toward sensor 308. Relay system 302 can be a constant magnification relay system, or can be configured to modify the magnification of a relayed image. An objective system (not shown) produces a right side intermediate image 320 on a focal plane 322, thereby enabling sensor 308 to detect the image. Dynamic mirror 304 and fixed mirror 306, together, form a folded optical path between relay system 302 and sensor 308. Dynamic mirror 304 and relay system 302 can be translated along arrow 324 for changing the parallax or stereoscopic system 300. Thus, intermediate image 320 is relayed by relay system 302 toward dynamic mirror 304, and from dynamic mirror 304 via fixed mirror 306 toward the right side of sensor 308. Mirror 304 is dynamic to change the parallax of the system. It can be a fixed mirror for systems not requiring dynamic change of the parallax. In addition, other elements can be designed to be dynamic instead or in addition to mirror 304.

With reference to FIG. 3B, stereoscopic system further includes a beam splitter 310, optically coupled between mirror 306 and sensor 308, and an IR sensor 312. Beam splitter splits the relayed image such that it is detected by both sensor 308 and sensor 312. It is noted that IR sensor can be replaced by any other secondary sensor, such as a UV sensor, a focus sensor (as detailed herein below with reference to FIGS. 5A-5C), a polarized light sensor, and the like. Accordingly, beam splitter is adapted to the type of secondary sensor 312. For example, in case of an IR sensor 312, beam splitter 310 is a dichroic splitter separating between visible light and IR light.

2.4 Robotic Arm Guidance

As detailed above, for example with reference to FIG. 1, the cameras of the microsurgery system of the disclosed technique are suspended in above the operating area for imaging the operated area from a far, thereby freeing the OR from physical obstructions associated with prior art surgical microscopes. As further mentioned above, the cameras can be mounted on a mounting frame, which can be moveable, such as moving robotic arm.

Figure 4:
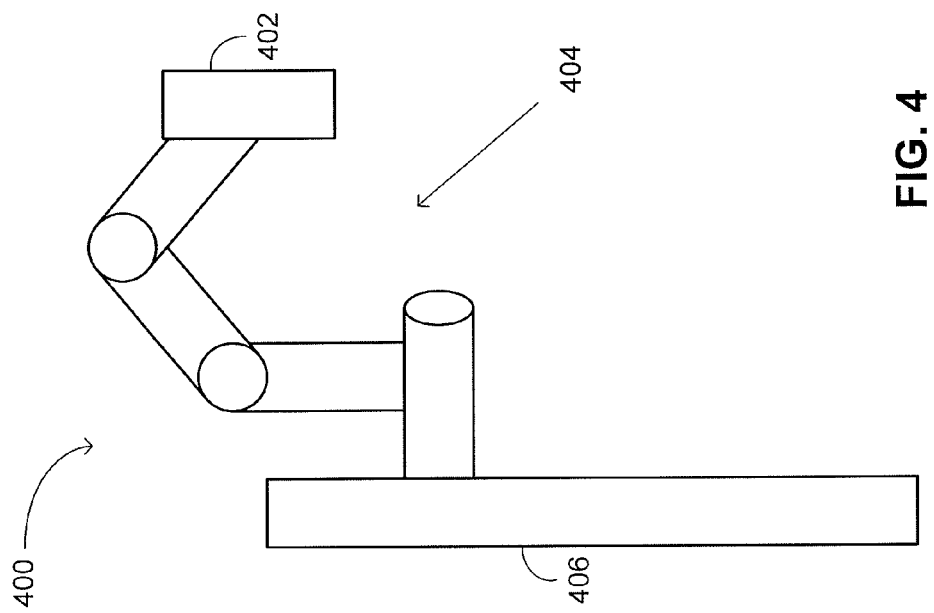
FIG. 4 is a schematic illustration of a mounted microsurgery system mounted on a robotic arm, constructed and operative in accordance with yet another embodiment of the disclosed technique.

Reference is now made to FIG. 4, which is a schematic illustration of a mounted microsurgery system, generally referenced 400, mounted on a robotic arm, constructed and operative in accordance with yet another embodiment of the disclosed technique. Mounted microsurgery system 400 includes a microsurgery system 402, a robotic arm 404, and a support pole 406. Microsurgery system 402 is mounted at the end of robotic arm 404, which in turn is mounted on support pole 406.

Microsurgery system 402 is a system for acquiring image sequences of an operated area, and for producing real-time magnified ROI sequences therefrom allowing a user to perform a microsurgery procedure (e.g., microsurgery system 100 of FIG. 1, or microsurgery system 200 of FIG. 2). Robotic arm 404 is a mechanical arm including a plurality of links coupled by joints actuated by actuators, which allow for various motions (e.g., rotational joints and linear joints). Robotic arm 404 moves microsurgery system 402 for allowing microsurgery system to capture sequences of the operated area from a range of perspectives. The control of robotic arm 404 would be detailed further herein below in the following paragraphs. Support pole 408 supports robotic arm 404 (and microsurgery system 402). Thereby, microsurgery system 402 is suspended above the operated area.

Robotic arm 404 can be guided automatically according to the movements of the user. Robotic arm 404 is coupled with the processing device of microsurgery system 402 (not shown). For example, a tracker (e.g., optical, electromagnetic and the like) is attached to the hand of the user, for tracking its motions. The processing device guides robotic arm 404 to move according to the motions of the hand of the user, such that the cameras of microsurgery system 402 (not shown) are imaging the operated area. In accordance with another example, the tracker is attached to the head of the user. Robotic arm 404 follows the users head for imaging the area that the user currently views. Microsurgery system 402 of the disclosed technique can further incorporate safety mechanisms to avoid unwanted robot arm movements. For example, rapid movements are not imitated by robotic arm 404, or an allowed motion box can be predefined for robotic arm 404 (from which it cannot extend).

2.5 Autofocus

Figure 5B:
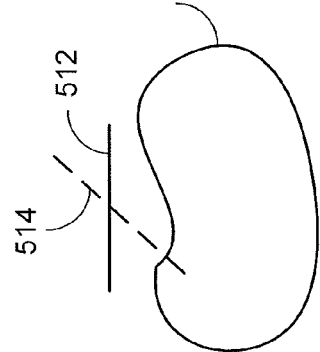
FIGS. 5A, 5B and 5C, are schematic illustrations of a focus-control system, constructed and operative in accordance with yet a further embodiment of the disclosed technique.
Figure 5C:
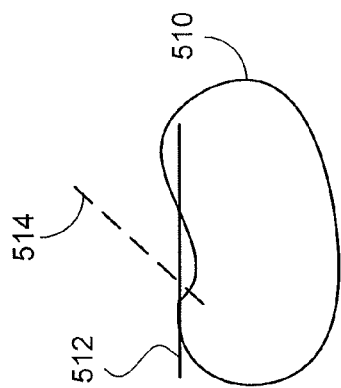
Figure 5A:
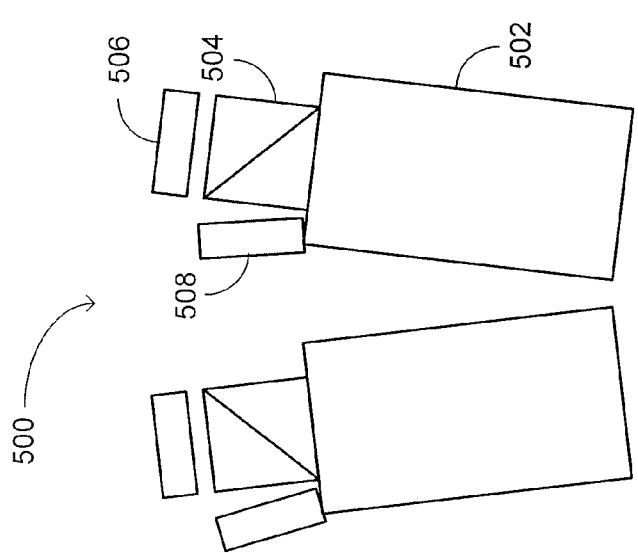

Reference is now made to FIGS. 5A, 5B and 5C, which are schematic illustrations of a focus-control system, generally referenced 500, constructed and operative in accordance with yet a further embodiment of the disclosed technique. FIG. 5A depicts the focus-control system. FIG. 5B depicts the focal planes of the image sensor and the focus-control sensor of the focus-control system of FIG. 5A, in case the imaged object is out of the image sensor focus range. FIG. 5C depicts the focal planes of the image sensor and the focus-control sensor of the focus-control system of FIG. 5A, in case the imaged object is within the image sensor focus range.

Focus-control system 500 is a stereoscopic system including two symmetric optical systems for acquiring two images from slightly different perspectives. For the sake of brevity, only the right optical system is indicated with reference numerals in FIG. 5A and would be detailed herein below. However, the right optical system includes the same elements and is operated in the same manner. Each of the optical systems (e.g., the right enumerated optical system and the left un-enumerated optical system) is also referred to herein as a camera system. It is noted that the autofocus control mechanism described herein below can be applied to a single camera (and not only to stereoscopic cameras). That is, the autofocus mechanism described below for the right optical system can operate independently for adjusting the focus of single optical system.

Focus-control system 500 is configured to control the focus of an optical system such that an imaged object (e.g., object 510 of FIGS. 5B and 5C) would be positioned within the focusing range of the image sensor. Focus-control system 500 can be implemented in any imaging system having modifiable focus range. For example, focus-control system can be implemented within the microsurgery system of the disclosed technique.

Focus-control system 500 includes a lens 502, a beam splitter 504, an image sensor 506 and a focus-control sensor 508. Lens 502 is optically coupled with beam splitter 504, which in turn is optically coupled with each of image sensor 506 and focus-control sensor 508. Focus-control system 500 further includes a focus-modifying subsystem (not shown) and a controller (e.g., processing device 106 of FIG. 1, or processing device 206 of FIG. 2).

Lens 502 is an objective lens (or group of lenses) for producing an image of the object onto imaging sensor 506. Beam splitter 504 is an optical element for splitting the light rays constituting the object image produced by lens 502, thereby producing two object images. Beam splitter 504 directs one object image toward image sensor 506, and the other object image toward focus-control sensor 508. Image sensor 506 is positioned coaxially with lens 502 and acquires the object image produced by lens 502.

Focus-control sensor 508 provides input to the controller for controlling the focus-modifying subsystem for modifying the focus of system 500 of image sensor 506. Focus-control sensor 508 is tilted with respect to the optical axis of lens 502 (i.e., more precisely tilted with respect to the folded optical axis of lens 502 after being folded by beam splitter 504). Thereby, only a portion (e.g., a row) of focus sensor 508 is in focus. By determining which row of focus sensor 508 is in focus, the controller can determine the desired focus characteristics for the image sensor (e.g., determine the desired focal plane and the depth of field).

The controller can determine which row of focus-control sensor 508 is in focus by various methods, such as the row having the maximum intensity, the row associated with maximal gradients. Accordingly, the controller determines the desired focus characteristics, and operates focus-modifying subsystem.

It is noted that in a stereoscopic system (composed of two cameras), it is important that the change in focus in both cameras is coordinated to prevent viewer fatigue and discomfort. That is, it is important that both cameras change focus at the same rate and focus on the same object plane. Focus-control system includes a focus-control sensor for each image sensor, thereby allowing the controller to coordinate the focus characteristics of the image sensors. In accordance with an alternative embodiment of the disclosed technique, only one of the image sensors (e.g., the left eye system) includes a focus-control sensor, and the controller adjusts the focus of both image sensors according to the data provided by the single focus-control sensor.

In the example set forth herein above with reference to FIGS. 5A-5C, an autofocus mechanism was coupled with each of a stereoscopic pair of cameras. It is noted however that the autofocus mechanism can operate in a similar manner for a single camera as well. Additionally, the autofocus mechanism can be employed for controlling the focus of any lens system, whether coupled to a camera or not. That is, by directing light focused by the lens system toward a tilted image sensor, and determining which portion of the image sensor receives a focused image, the autofocus mechanism can control the focus of the lens system.

2.6 Optical Tissue Penetration Module

Figure 6:
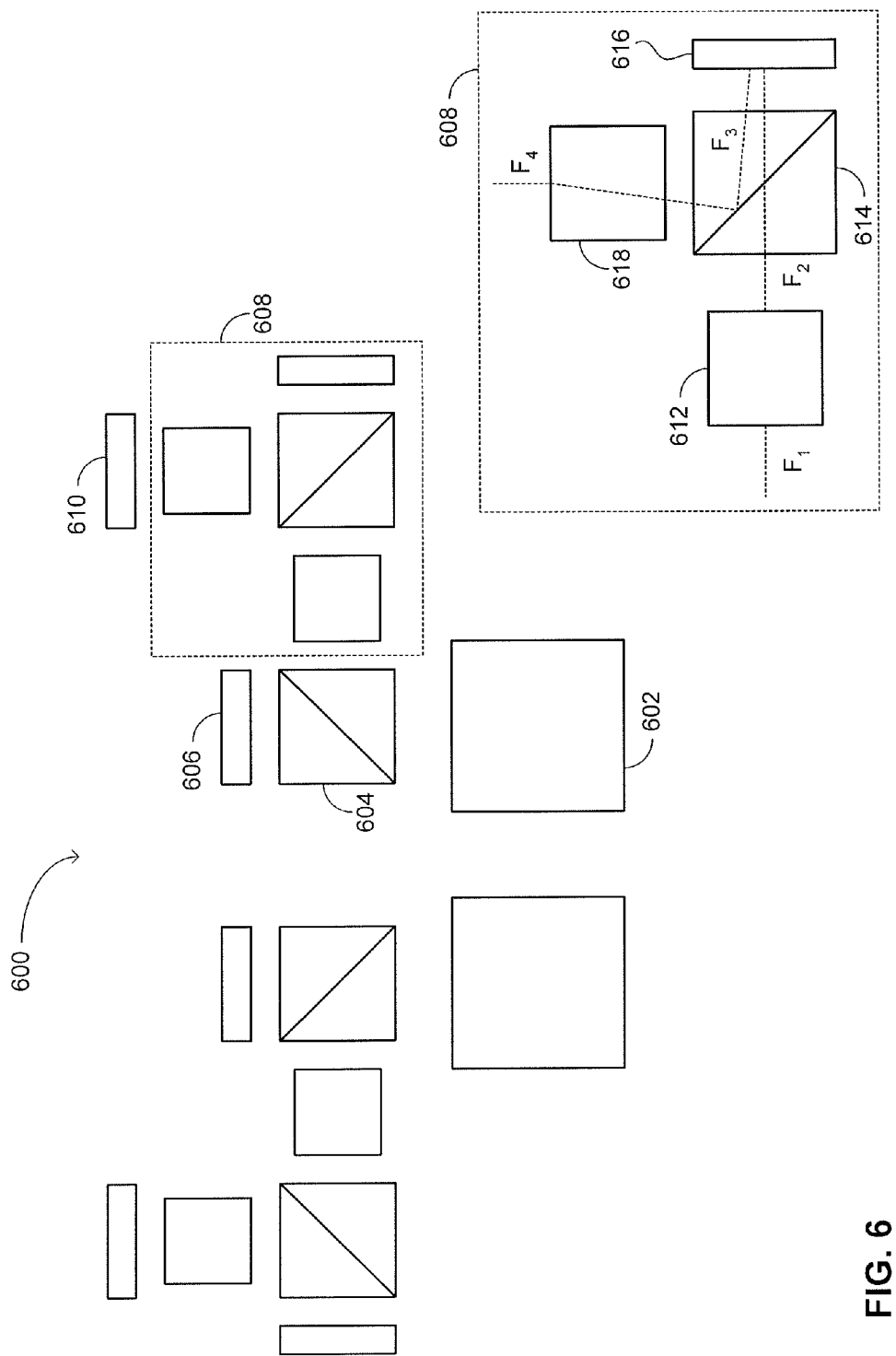
FIG. 6 is a schematic illustration of a tissue-penetration system for imaging subcutaneous tissues, constructed and operative in accordance with yet another embodiment of the disclosed technique.

In accordance with another embodiment of the disclosed technique, each of the cameras of the microsurgery system of the disclosed technique can be complemented with a tissue-penetration module. The tissue-penetration module acquires an image of the subcutaneous tissues (e.g., image penetration of few millimeters) while the main image sensor acquires an image of the external tissues. Reference is now made to FIG. 6, which is a schematic illustration of a tissue-penetration system, generally referenced 600, for imaging subcutaneous tissues, constructed and operative in accordance with yet another embodiment of the disclosed technique.

Tissue-penetration system 600 includes a microscope lens 602, a beam splitter 604, a first image sensor 606, a 4f & deconvolution module 608 and a second image sensor 610. The components of 4f & deconvolution module 608 are shown in the magnified box, and include a first optical assembly 612, a total internal reflector 614, a Digital Micromirror Device (DMD) 616 and a second optical assembly 618. Microscope lens 602 is optically coupled with beam splitter 604. Beam splitter 604 is optically coupled with both first image sensor 606 and with 4f module 608. 4f module 608 is further optically coupled with second image sensor 610.

Microscope lens 602 is a lens or a group of lenses (or other optical elements) configured to receive light from a target area and to focus the light, thereby producing an image of the focused area. For example, microscope lens 602 can be a lens positioned in front of the cameras of the imaging system of the claimed invention (e.g., imaging system 100 of FIG. 1 or imaging system 200 of FIG. 2). Microscope lens 602 transmits the focused light toward beam splitter 604.

Beam splitter 604 splits the target area image received from microscope lens 602 (i.e., splits the light focused by lens 602) and directs a first image toward first image sensor 606 and a second image toward 4f module 608. Thereby beam splitter 604 splits the optical axis of system 600 into two optical branches. In particular, beam splitter 604 is a dichroic beam splitter that directs visible light toward first image sensor 606, and reflects IR light toward 4f module 408. That is, tissue-penetration system 600 includes a visible imaging channel and a tissue-penetration channel which are branching at beam splitter 604.

First image sensor 606 is an image sensor for acquiring the image of the target area that is focused by microscope lens 602. Image sensor 606 detects the image composed of the visible light transmitted by beam splitter 604. Image sensor 606 is a high resolution image sensor similar to the image sensors of the cameras detailed herein above with reference to FIGS. 1 and 2.

4f & deconvolution module 608 serves as an analog filter for filtering out spatial image frequencies. For example, when imaging a selected subcutaneous tissue layer, 4f module 608 filters out strong reflections from the skin, appearing as DC in frequency domain, and transmits to image sensor 610 the high frequencies of the reflected from the tissue to be imaged. The components of 4f module 408 are depicted in the magnified box at the bottom right corner of FIG. 6, and would be detailed further herein below.

Second image sensor 610 is an image sensor for acquiring an IR image transmitted by 4f module 608. The IR image can be composed of light reflected from subcutaneous tissues at the target area and thereby second image sensor 610 acquires an image of the subcutaneous tissues. The IR light reflected from the subcutaneous tissues is produced by an IR light source (not shown), and can be of various IR wavebands, such as, Near IR (NIR). For example, the IR light can be of frequencies between 700-1000 nm. In accordance with other embodiments of the disclosed technique, frequencies between 1000-1700 nm can also be used. It is noted that lower frequencies (i.e., lower than 700 nm) penetrate the skin in a poorer manner. Higher frequencies (i.e., higher than 1700 nm) might be complicated by means of optics and detectors. Additionally, the absorbance of higher frequencies in fluids (e.g., blood) is more significant.

In this manner, imaging system 600 simultaneously acquires a visible image of the external tissue layer of the target area and an image of the subcutaneous tissues. Imaging system 600 presents both images to the user by employing a display. For example, the images can be overlaid, fused, or presented separately.

As mentioned above, 4f & deconvolution module 608 serves as analog spatial frequencies filter. The components of 4F module 608 are detailed in the following paragraphs. First optical assembly 612 is positioned such that the image of the target area focused by microscope lens 602 and reflected by beam splitter 604 falls on a focal plane of first optical assembly 612. First optical assembly 612 produces a Fourier transform of the image focused by lens 602 on the surface of DMD 616. That is, the focused image at an input plane of first optical assembly 612 (i.e., located at the input focal length of optical assembly 612) is transformed into a frequency domain image at the output plane of first optical assembly 612 (i.e., located at the output focal length of optical assembly 612). In this manner, first optical assembly 612 serves as an optical transform system.

DMD 616 is composed of an array of separately controllable small mirrors (size of micrometers or tens of micrometers) that can switch between "on" and "off" states. Specifically, in the "on" state the mirrors of DMD 616 reflects light toward second image sensor 610 (via reflector 614 and second optical assembly 618), and in the "off" state it reflects the light away from it. DMD 616 is positioned on a plane where optical assembly 612 produces a Fourier transform of the image (i.e., at the surface of DMD 616 the transformed focused image is presented in the frequency domain). DMD 616 functions as an analog spatial filter. That is, mirrors of DMD 616 which are turned off, filer out respective frequencies of the transformed focused image of the target area. DMD 616 filters out selected frequencies, for example, the DC of light reflected from the skin layer so that it will not blur a subcutaneous image. For example, the mirrors at the center of DMD 616 are set to their off state to serve as low pass filter. It is noted that, DMD 616 can be replaced by any other reflecting element capable of pattern changing.

Total internal reflector 614, reflects the light that was transmitted (i.e., not filtered out) by DMD 616 toward second image sensor 610. Total inner reflector 614 can be replaced by other reflectors that admit the image toward DMD 616 and reflect the transmitted filtered image from DMD 616 toward second image sensor 610. Second optical assembly 618 transforms the frequency domain image transmitted from DMD 616 back into image domain of the target area. Specifically, second optical assembly 618 focuses the back-transformed image on the surface of second image sensor 610.

The focus distance of 4f module 608 can be varied for imaging different layers of subcutaneous tissues. The focus distance is varied by moving 4f module 608, or elements thereof. Thereby, images of different tissues layers are detected by second image sensor 610. The received images are blurred and composed of reflections from the different tissue layers. System 600 employs 3D deconvolution to reconstruct sharp images of the different subcutaneous layers from the images detected by second image sensor 610.

It is noted that the imaged target area is lighted for the purpose of the tissue-penetration imaging. In accordance with another embodiment of the disclosed technique, the light source is a polarized light source (linear, circular or other) to eliminate some specular reflections. The imaging channel is polarized as well, in accordance to the light source, with different angle.

2.7 OCT

The cameras of the microsurgery system of the disclosed technique can be complemented by an Optical Coherence Tomography (OCT) channel, and in particular Fourier domain OCT. The OCT complemented system allows the user to view in real-time an OCT image perfectly aligned to the stereo image received by the microsurgery system. The OCT channel produces a set of images of various depths of subcutaneous tissues. Thus the OCT complimented microsurgery system allow presenting OCT images along with (e.g., overlaid on) the visible images of the external operated tissues. The OCT complimentary module is coupled to the microsurgery system via a beam splitter that splits the target area image received from microscope lens and directs a first image toward the image sensor of the microsurgery system and a second image toward the OCT module.

Fourier Domain Optical Coherence Tomography (FDOCT) is an imaging technique that operates by collecting signals related to different wavelengths of light, and using a mathematical relationship to generate an image. FDOCT extracts spectral information by distributing different optical frequencies onto an image detector via a dispersive element. Thereby the information of the full depth scan can be acquired within a single exposure.

2.8 Parallax Control

Figure 7:
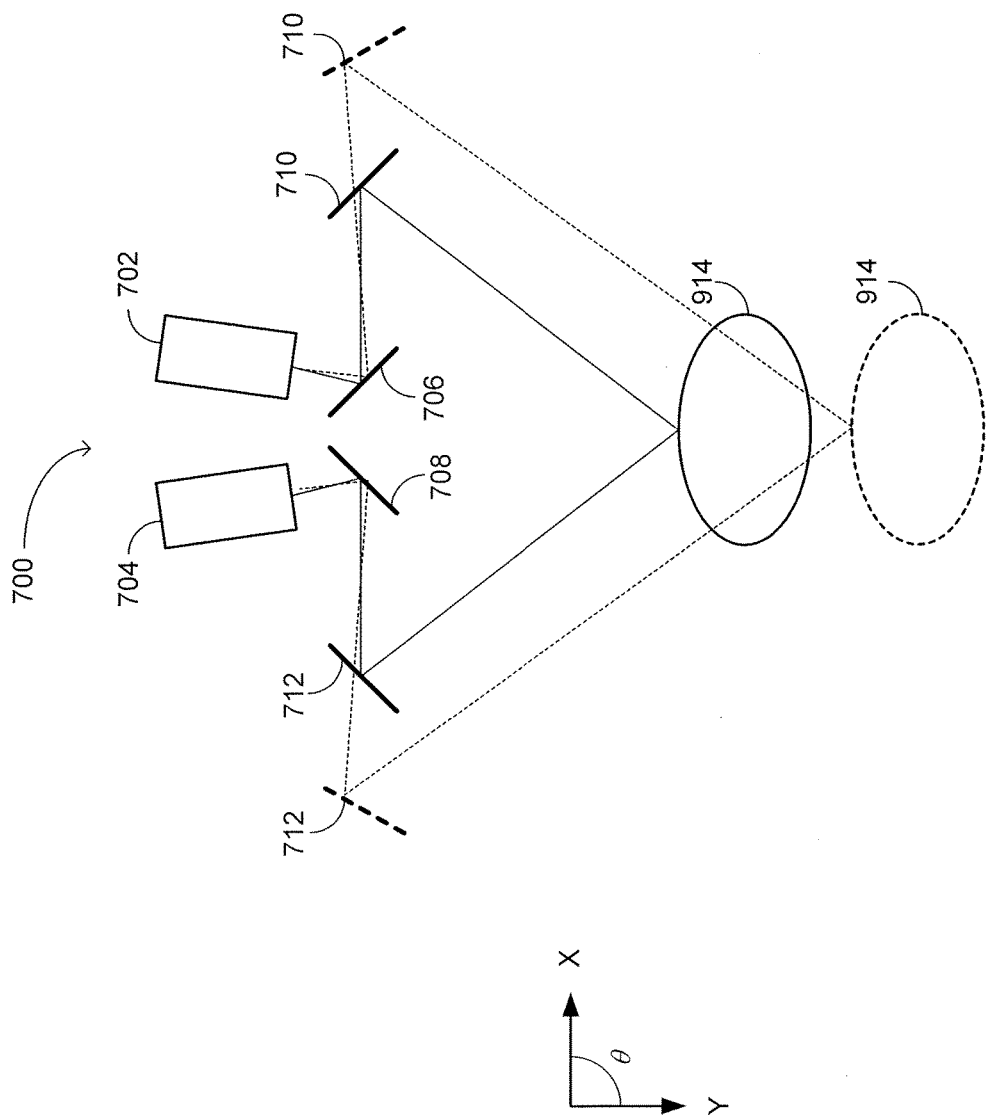
FIG. 7 is a schematic illustration of a microsurgery system, which parallax can be adjusted, constructed and operative and accordance with yet a further embodiment of the disclosed technique.

As seen, for example, in FIG. 1, the microsurgery system of the disclosed technique includes two cameras for acquiring stereoscopic image sequences of the operated area. In accordance with another embodiment of the disclosed technique the parallax between the cameras can be adjusted. The adjustable parallax mechanism is employed for situations in which the imaging angle between the cameras should be dynamically changed during an operation. Reference is now made to FIG. 7, which is a schematic illustration of a microsurgery system, generally referenced 700, which parallax can be adjusted, constructed and operative and accordance with yet a further embodiment of the disclosed technique. Microsurgery system 700 includes a pair of cameras 702 and 704, a pair of fixed mirrors 706 and 708, and a pair of moveable mirrors 710 and 712.

Cameras 702 and 704 are substantially similar to cameras 202 and 204 of FIG. 2. Fixed mirrors 706 and 708 are reflectors fixed in place with respect to cameras 702 and 704. Moveable mirrors 712 and 710 can be moved along the X axis and can rotate at an angle θ (i.e., rotate around an axis perpendicular to the plane of FIG. 7). In this way, moveable mirrors 712 and 710 adjust the parallax between cameras 702 and 704, to control stereopsis comfort. The rotation of moveable mirrors 710 and 712 can be mechanically adjusted in accordance with the movement along the X axis. The movement in both ways (i.e., horizontal movement and rotation) can be set as a function of the object distance, the focus level, or a user interface selection. In accordance with another embodiment of the disclosed technique, a light source can also be diverted using the moveable mirrors. For example, the illumination beam of a coaxial light source illuminating the LOS of the cameras is folded by the mirrors as is the LOS of the cameras.

In the example depicted in FIG. 7, moveable mirrors 710 and 712 are depicted in two configurations, one depicted in solid line and another in dotted line. The solid depiction of moveable mirrors 710 and 712 depicts the parallax for an object 714 positioned at a first distance from the cameras. The dotted depiction of moveable mirrors 710 and 712 depicts the parallax for object 714 positioned at a second distance from the cameras. As can be seen, the parallax angle of the solid line is equal for the parallax angle of the dashed line, relating object 714 solid and dashed appropriately.

2.9 DMD Light Source

In accordance with another embodiment of the disclosed technique, the lighting system can include a shutter module. A light source produces an illumination beam which passes through the shutter module on its way to the target area (e.g., the operated area). The shutter module blocks (or at least attenuates) some portions of the illumination beam, thereby creating uneven illumination. In this manner, the shutter module allows for illuminating different portions of the target area in different manners.

Figure 8C:
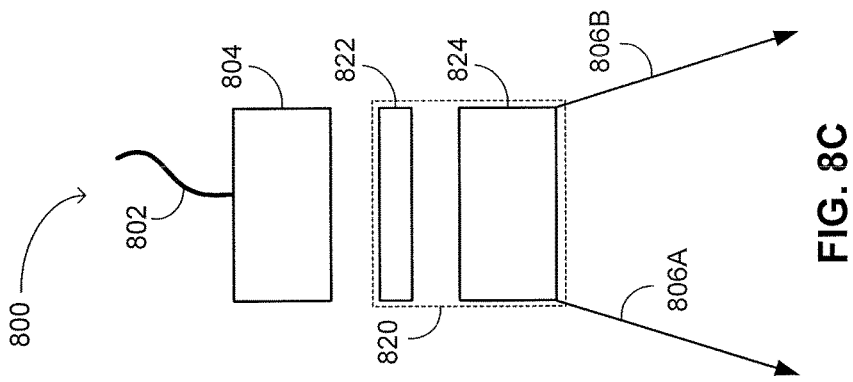
FIGS. 8A-8E are schematic illustrations of a lighting system including a shutter module, constructed and operative in accordance with yet another embodiment of the disclosed technique.
Figure 8B:
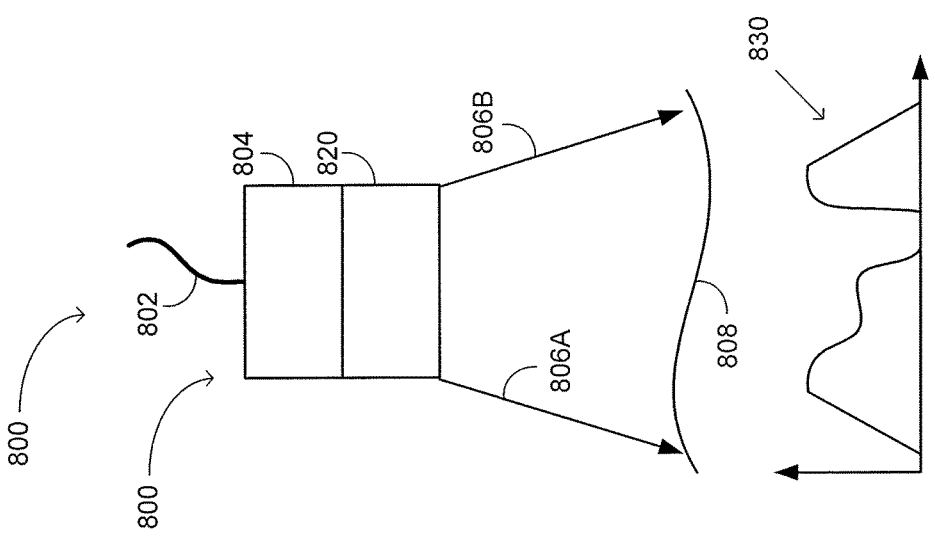
Figure 8A:
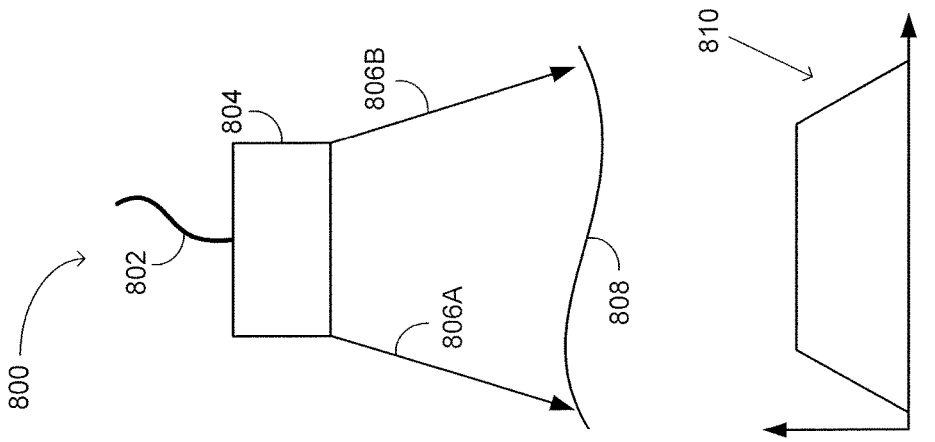
Figure 8E:
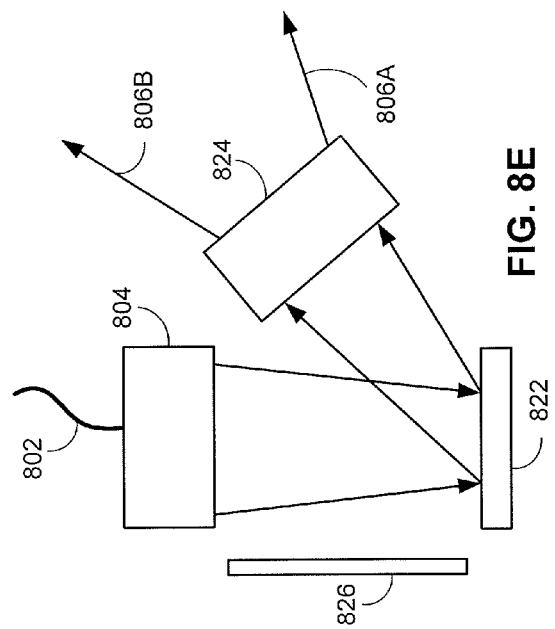
Figure 8D:
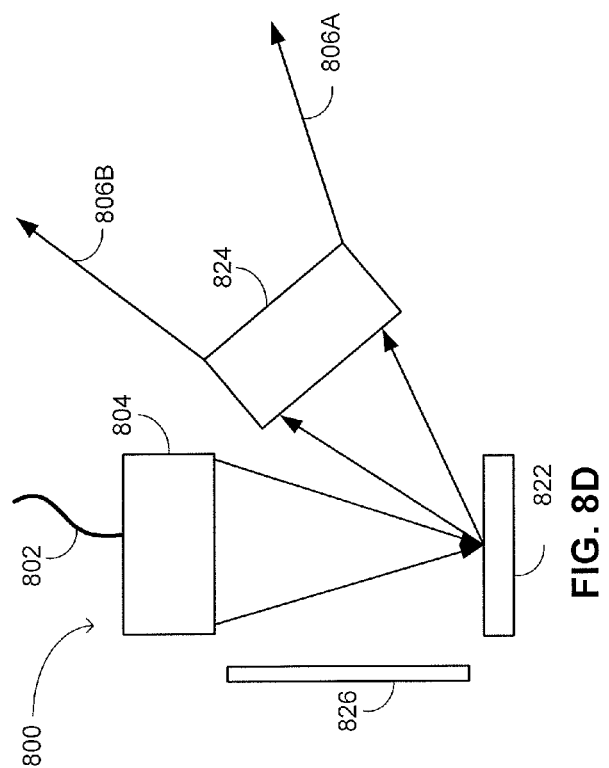

Reference is now made to FIGS. 8A-8E, which are schematic illustrations of a lighting system including a shutter module, generally referenced 800, constructed and operative in accordance with yet another embodiment of the disclosed technique. FIG. 8A depicts a lighting system without a shutter module. FIG. 8B depicts a lighting system having a shutter module. FIG. 8C depicts a lighting system having a shutter module, which light passes through. FIG. 8D depicts a lighting system having a reflective shutter module, positioned in the focal plane of an optical module. FIG. 8E depicts a lighting system having a reflective shutter module, positioned out of the focal plane of an optical module.

With reference to FIG. 8A, lighting system 800 includes a light source 802 (e.g., an optical fiber transmitting light from a light source, LED source or any other light source) and an optical module 804. Light source 802 provides an illumination beam to optical module 804, which directs the illumination beam toward target area 808. The illumination beam is represented by light beam 806A and 806B. Optical module 804 can further increase the output angle of the illumination beam, diffuse the illumination beam or shape it in other manners known in the art. A graph 810 depicts the illumination level (the vertical axis) as a function of the location in the target area (i.e., the horizontal axis). As can be seen in Graph 810 of FIG. 8A, the illumination level is even across the target area.

With reference to FIG. 8B, a shutter module 820 is added to lighting system 800. Shutter module 820 is positioned between optical module 804 and target area 808. Shutter module 820 receives the illumination beam and selectively attenuates (or blocks) portions of the illumination beam. Thereby, the microsurgery system of the disclosed technique can employ lighting system 800, including the shutter module, for selectively controlling illumination levels of different portions of the target area. A graph 830 depicts the illumination level (the vertical axis) as a function of the location in the target area (i.e., the horizontal axis). As can be seen in Graph 830 of FIG. 8B, the illumination level of different portions of the target area is uneven. That is, some portions receive higher levels of illumination, and some portions don't receive any illumination at all.

In this manner, the shutter module of the lighting system allows for selectively adapting the illumination level of different portions of the target area to various applications.

For example, a highly reflective area of the target area (e.g., covered with a mucosal layer) can receive lower illumination levels to avoid blinding or to improve the dynamic range of the cameras of the microsurgery system.

With reference to FIG. 8C, shutter module 820 (depicted in a dotted line) includes a shutter array 822 and optical elements 824. Shutter array 822 can selectively attenuate different spatial portions of the illumination beam passing therethrough. Optical elements 824 receive the selectively-spatially-attenuated illumination beam and direct it to the target area. Optical elements 824 can shape the selectively-spatially-attenuated illumination beam, for example, by increasing the output angle of the beam, diffusing the beam, and the like.

With reference to FIG. 8D, the shutter module includes a reflective shutter array 822, optical elements 824. Reflective shutter array 822 can be for example, a DMD, or another pattern reflector. Reflective shutter array 822 can selectively reflect different spatial portions of the illumination beam toward optical elements 824 or deflect them in another direction, such that portions of the illumination beam would not reach the target area. The shutter module can further include a black screen 826 toward which unwanted portions of the illumination beam can be directed, and for preventing outside light from reaching optical elements 824. Optical elements 824 receives the reflected illumination beam (i.e., those portions which were selectively reflected toward optical elements 824 by reflective shutter array 822) and direct it to the target area. In the example set forth in FIG. 8D, reflective shutter array 824 is located at the focal plane of optical module 802.

With reference to FIG. 8E, reflective shutter array 824 is located out of the focal plane of optical module 802, such that shutter array 824 receives a collimated (or semi-collimated) illumination beam, and selectively reflects spatial portions of the illumination beam toward optical elements 824.

3 Optional HMD Structure

The processing device of the microsurgery system of the disclosed technique (e.g., microsurgery system 200 of FIG. 2) provides image sequences to the HMD, possibly including overlaid data and symbols. The HMD can include several display components, for example, for displaying a central high resolution image and a peripheral lower resolution image (as would be detailed further below with references to FIGS. 9A-9C), the processing device provides the necessary image or control instructions to each display component. The HMD can include display components such as micro-displays, scanning mirrors, Digital Micro-mirror Device (DMD), and the like.

A see-through HMD may be used in some embodiments, thus allowing image sequences to be superimposed on a real-world view (though magnified images are not superimposed on an unmagnified real-world view). The see-through HMD enables any of the following exemplary applications:

Switching between the projected video to real world by varying the see-through opacity.

Maintaining semi-transparency in the see-through opacity and by that showing real world and video.

Overlaying video on the real world, and by so providing augmented reality.

In accordance with another embodiment of the disclosed technique, the transparency of the display can be controlled. A shutter mechanism coupled with the display can block (or attenuate) the outside scene image passing through the see-through display. When the shutter is open the projected image (e.g., acquired by the cameras) is overlaid on the outside image. When the shutter is closed, the outside image is blocked, and the viewer sees only the projected image. By closing the shutter, the contrast of the projected image is increased. The shutter can be either mechanical or electronic, or any other shutter type. The shutter can be manually or automatically activated. For example, the user can turn the shutter on and off (or control the degree of attenuation of the outside image) by an interface, such as a control button, via voice activation, or via head motion activation. For instance, when the user turns her head by more than 25 degrees (as determined by the tracker), the shutter is opened to allow the user to view her surroundings. The shutter attenuation can change gradually with the movements of the head of the user, or change abruptly at a predefined threshold (i.e., step function). The transparency change can be made on part of the see-through display or all of it. Transparency may be adjusted according to user manual selection and/or ambient light thresholds.

In accordance with another embodiment of the disclosed technique the displayed images of the HMD are focused to infinity. The focus to infinity provides the viewer relaxed effort for the eye and is less exhausting. In accordance with yet another embodiment, in case the HMD is a see-through HMD, and as the real world objects are not located at infinity (but within the OR), the focus of the HMD is set to the objects distance. The HMD can utilize a dynamic focus mechanism, setting the projected image focus distance to the viewer eye focus distance (or to the distance of the object that the viewer sees).

The transparency change of a see-through HMD can be made using passive or active coating or pads on the see-through display. The coating or pads are placed on a display element which is in the user line of sight. For example, it can be placed on a visor, a combiner, a waveguide or any other optical element used for the see-trough display. Passive coating can be activated to decrease the see-through display transmission by using Ultraviolet (UV) or IR illumination. Active coating can be electrically activated to decrease transmission.

The HMD of the disclosed technique produces high quality image sequences, which must be acceptable for the user (when compared to the image viewed through the eyepiece of a conventional surgical microscope. Put another way, the optical parameters of the HMD should be good enough to satisfy human vision parameters. The FOV of human vision is wide, yet the human IFOV (or visual acuity) varies with the location of the image on the retina. In particular, there is a relatively small area of the retina (i.e., relatively small FOV) with improved visual acuity. This area of the retina is called the fovea, and covers about two degrees of the FOV. When drawing away from the fovea the visual acuity degrades. A human viewer will not notice improvement in resolution, or have the ability to see more details, by displaying images that allow for smaller IFOV than that of the human vision. Therefore, images projected on the periphery of the retina surrounding the fovea, can be of reduced resolution (with respect to the images projected on the fovea), without compromising the acuity of the image perceived by the observer.

It is common to refer the measurement of the limiting visual acuity on shapes, gratings, points etc. For a normal young healthy person, having good sight, the eye can identify two small points on uniform background (where the points are black and the background is white) when the angle separating them is larger than 1 arcmin (1 arcmin, or minute of arc, equals roughly 0.000291 rad). When a healthy person observes grating pattern (white bar next black bar, with repeating pattern), the eye can identify the bars as long as the angle between them is larger than 2 arcmin. Many factors influence the visual acuity and may degrade it—like the scene brightness, distance of image from the center of fovea, the age of person, the contrast of target, stability of the image etc. The pupil diameter also effects the visual acuity significantly (effects the diffraction of the eye and the optical aberrations). Taking into consideration all of the parameters effecting visual acuity it is common to say that a healthy human visual acuity is in the range of 1 arcmin to 2 arcmin (0.000291 to 0.000582 rad).

Figure 9A:
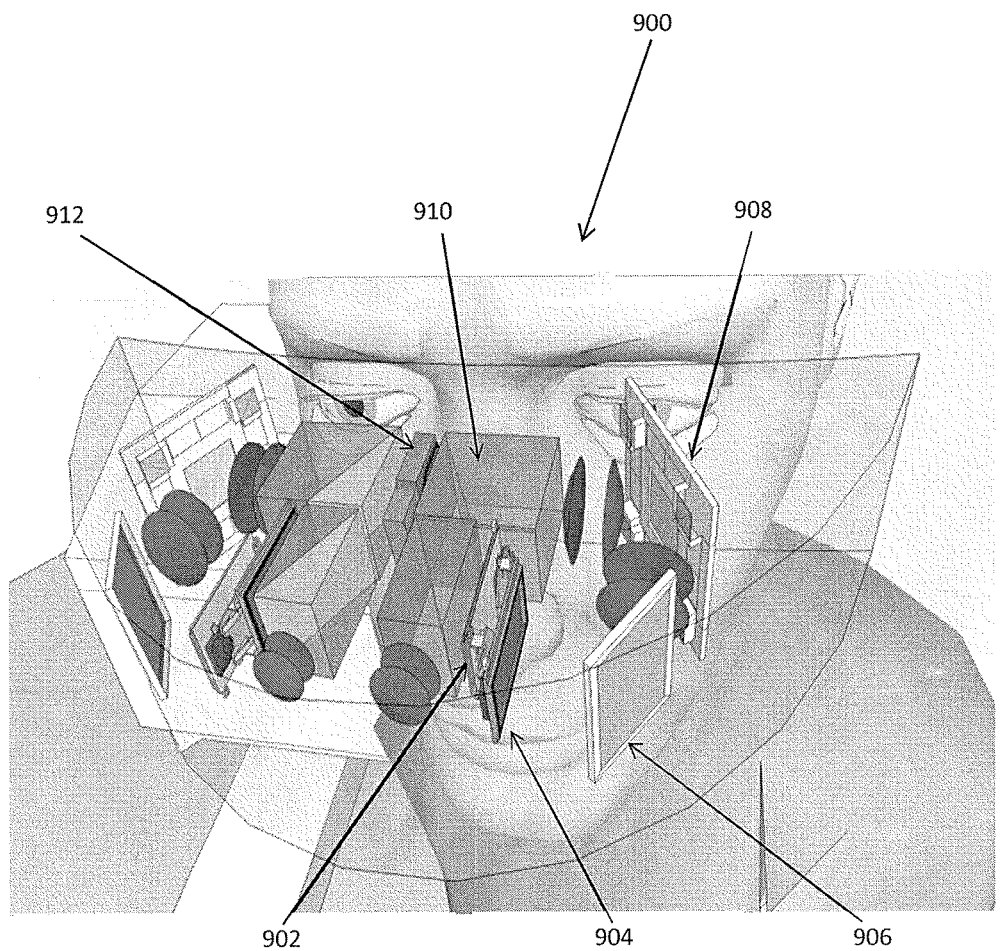
FIGS. 9A, 9B and 9C, are schematic illustrations of an HMD for displaying a high resolution image to the fovea and displaying a lower resolution image to the periphery of the eye of the user, constructed and operative in accordance with yet another embodiment of the disclosed technique.
Figure 9B:
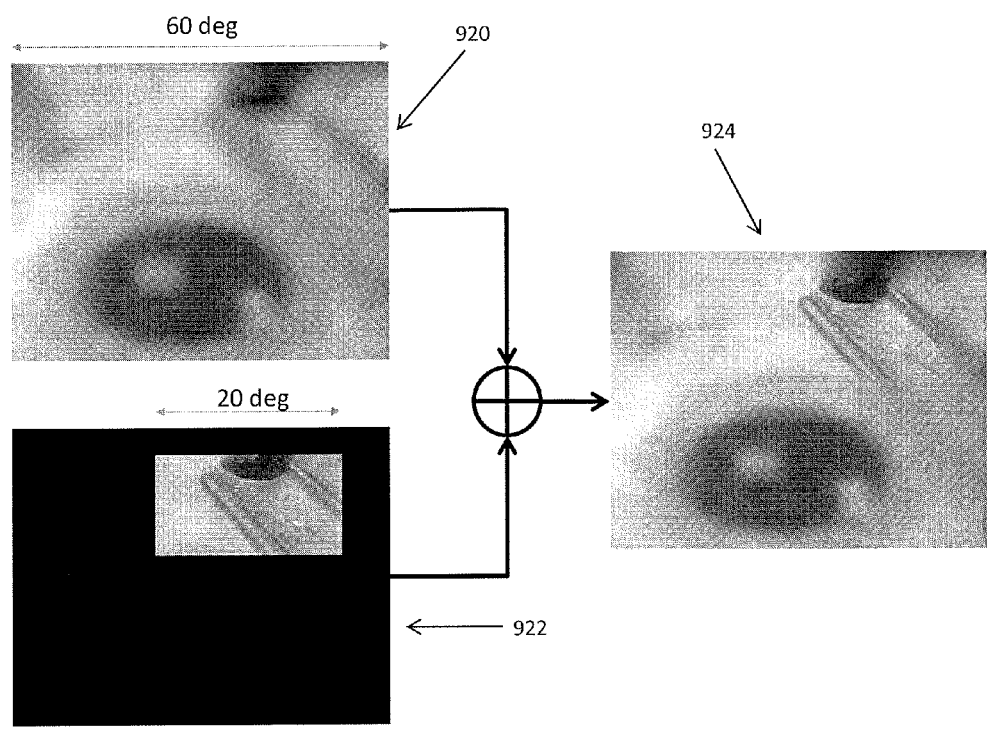
Figure 9C:
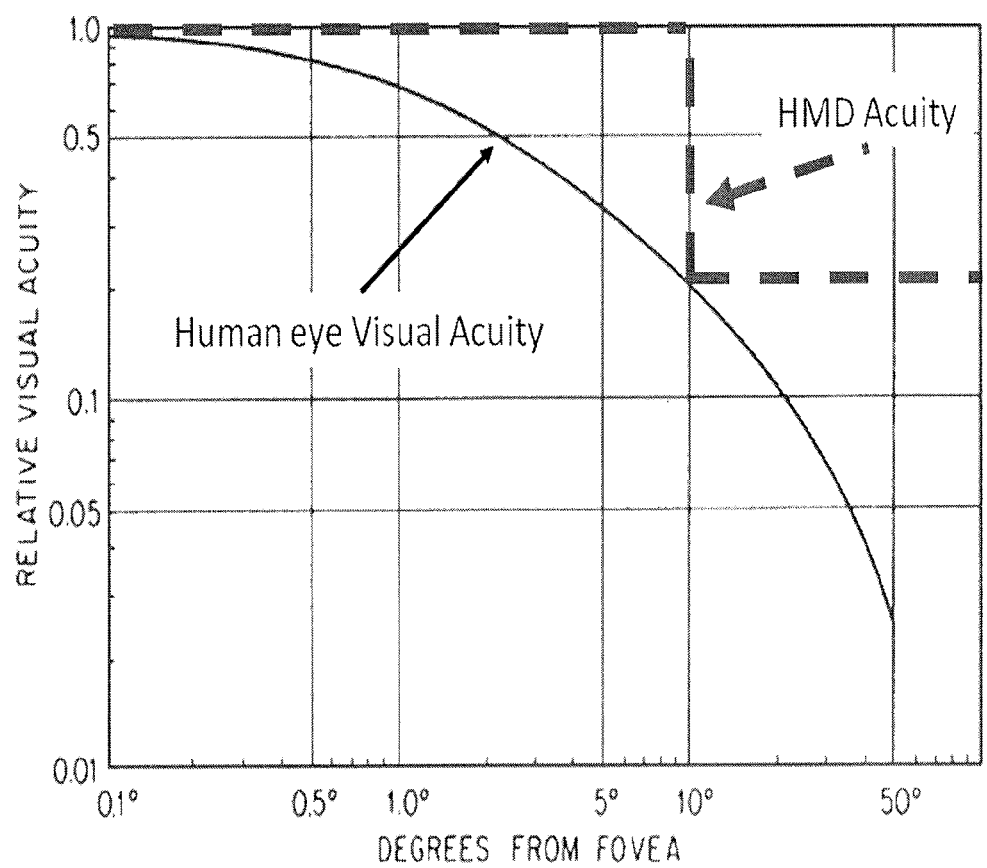

Reference is now made to FIGS. 9A, 9B and 9C, which are schematic illustrations of an HMD, generally referenced 900, for displaying a high resolution image to the fovea and displaying a lower resolution image to the periphery of the eye of the user, constructed and operative in accordance with yet another embodiment of the disclosed technique. FIG. 9A depicts HMD 900. FIG. 9B depicts the fovea image the periphery image and the combined image of HMD 900 of FIG. 9A. FIG. 9C depicts a relative visual acuity scheme of a human eye.

With reference to FIG. 9A, HMD 900 is an exemplary HMD providing varying resolution images adapted to the varying IFOV of the human eye within its FOV. In particular, HMD 900 displays a high resolution image to the fovea, and displays a lower resolution image to the peripheral portions of the eye of the user. HMD 900 is a dual-eye HMD including a pair of micro-display systems, one for each eye. Each micro-display system includes a peripheral display 902, a fovea display 904, a fixed mirror 906, a scanning mirror 908, an optical combiner 910 and an eye tracking camera 912. Peripheral display 902 is optically coupled with optical combiner 910. Fovea display 904 is optically coupled with optical combiner 910 via fixed mirror 906 and scanning mirror 908.

Each of displays 902 and 904 can be any micro-display, such as an LCD, an Organic Light-Emitting Diode (OLED) or a Liquid Crystal on Silicon (LCOS). Additionally, each display can include additional optical elements, such as Digital Micro-mirror Device (DMD), a Digital Light Processing (DLP), scanning mirrors or any other method. Peripheral display 902 projects a peripheral image, and fovea display 904 projects a fovea image, both received from a processing device of a microsurgery imaging system (e.g., system 100 of FIG. 1 or system 200 of FIG. 2). Peripheral display 902 and the fovea display 904 are combined via optical combiner 910. The peripheral image, the fovea image and the combined image are detailed further herein below with reference to FIG. 9B.

The FOV of Fovea display 904 is narrow with respect to the FOV of peripheral display 902. However, the resolution of the fovea image is larger than that of the peripheral image. Put another way, the IFOV of fovea display 904 is smaller than that of peripheral display 902. The fovea image is moved according to the LOS of the viewer, as detected by eye tracking camera 912. For example, the fovea image is shifted by using a rotating mirror (e.g., actuated by MEMS). The rotating mirror (e.g., rotating around 2 Axes) is enslaved to the LOS of the viewer. The fovea image sequences directed to the fovea are substantially centered around the tracked LOS of the user. It is noted that HMD 900 can include any other functionality, or combination of functionalities, as detailed herein above with reference to HMD 209 of FIG. 2 and with reference to any HMD detailed in this application.

With reference to FIG. 9B, a peripheral image 920 and a fovea image 922 are combined into a combined image 924. As can be seen in FIG. 9B, fovea image 922 is smaller than peripheral image 920 (i.e., occupies a smaller portion of the combined image displayed to the user). On the other hand, the resolution (or acuity) of fovea image 922 is larger than that of peripheral image 920. Specifically, the image resolution of fovea image 922 (and the distance of the fovea display from the eye) allows an IFOV smaller or approximately equal to that of the human fovea, or at least comparable thereto (i.e., better angular resolution than that of the human eye). Similarly, the image resolution of peripheral image 924 (and the distance of the peripheral display from the eye) allows an IFOV smaller than that of the human peripheral retinal areas, or at least comparable thereto.

For example, in accordance with one embodiment of the disclosed technique, the processing device of the microsurgery system produces fovea image sequences allowing for IFOV smaller than 0.000592 radians. In accordance with another example, the FOV within which the fovea image sequences are viewed can be at least 2°.

To achieve better transition between the two superimposed images some smoothing can be done in the stitching area. For example, in the edges of fovea image 922, the resolution can be degraded monolithically (e.g., using image processing smearing) down to the resolution of peripheral image 920. Thereby, the combined image looks more natural.

As can be seen in FIG. 9C, displaying two grades of images, a high grade to the fovea and a lower grade to the periphery, will not compromise the acuity of the image perceived by the user. This is because the high grade image projected on the fovea allows for IFOV comparable with (or better than) that of the user in the fovea, and the lower grade image projected on the periphery also allows for IFOV comparable with (or better than) that of the user in the peripheral areas of the retina. In the example set forth in FIG. 9C, the high grade image is projected within 10° of the fovea, and the lower grade image is projected onto retinal areas which are further than 10° from the fovea.

3.1 Dynamic Eye Piece Parallax Control

In accordance with another embodiment of the disclosed technique, where the display (e.g., HMD 108 of FIG. 1 or HMD 208 of FIG. 2) includes a separate display for each eye of the user, the controller (i.e., the processing device) can adjust the display parallax to correspond to the user comfort. Prior art conventional surgical microscopes include fixed eyepieces, which are fixed in space. The fixed eyepiece compels the user to fix her head for long time periods in a stressed position. Minor head movements may cause image degradation starting with image vignette, blurring and complete loss of image.

Reference is now made to FIGS. 10A and 10B, which are schematic illustrations of a display system, generally referenced 1020, having adjustable eyepieces, constructed and operative in accordance with yet a further embodiment of the disclosed technique. Display system 1020 is a display having eyepieces (and is not an HMD). Thus, display system 1020 can be used for any system having eyepieces, such as a microscope having eyepieces.

With reference to FIG. 10A, a user views a displayed image (not shown) via eyepiece 1004. Specifically, the user directs her eye 1002 toward eyepiece 1004. The LOS of eye 1002 is indicated by 1006. The optical axis of eyepiece 1004 is indicated by 1008. For the user to view the displayed image, LOS 1006 should be substantially coaxial with optical axis 1008, and eye 1002 should be close enough to eyepiece 1004.

The adjustable eyepiece system of the disclosed technique aligns itself with the eyes of the user when the user places her head within a predefined motion box. The motion box is defined as the area that is limited by the range of eyepiece motion or by the detection range of a head or an eye tracker. With reference to FIG. 10B, adjustable eyepiece system 1020 includes an eyepiece support frame 1022 and a pair of eyepieces 1024. Eyepieces 1024 are incorporated into eyepiece support frame 1024. Eyepiece support frame 1022 further supports the optical channels leading to eyepieces 1024. Each optical channel relays to each of eyepieces 1024, a respective image to be displayed, and can further relay an outside scene image, onto which the display image is overlaid.

Eyepiece support frame 1022 allows adjusting the eyepieces position by moving along three axes –X, Y and Z, as seen in the Figure. Thereby, the position of eyepieces 1024 can be adjusted to the position of the eyes of the user. Additionally, eyepiece support frame 1022 allows directing eyepieces 1024 by rotating at angles θ, φ and ω, as seen in the Figure. Thereby, the optical axes of eyepieces 1024 can be adjusted to the LOS of the user. Further additionally, eyepiece support frame 1022 allows varying the Intermediate Pupil Distance (IPD) of eyepieces 1024, for adjusting it to the IPD of the user.

The alignment of eyepiece support frame 1022, and thereby of eyepieces 1024, is controlled according to the position and orientation of the eye of the user as determined by the tracker. In accordance with one embodiment of the disclosed technique, the eyepiece alignment is performed once at the beginning of the surgical operation. Alternatively, in accordance with another embodiment, the head of the user is continuously tracked, and the eyepieces are aligned accordingly throughout the procedure. In the dynamic adjustment of the eyepieces, limitations can be defined for preventing the system from moving rapidly. For example, when the user moves her head sideways by an extent exceeding a threshold (e.g., to see other things in the OR), system 1000 does not move the eyepieces with the head of the user.

For moving and directing eyepieces 1024, eyepiece support frame 1022 can be a motorized stage, a gimbal, a robotic arm and the like. Support frame 1022 moves and rotates eyepiece 1024 according to instructions from a controller. The controller receives input respective of the head position and orientation from the head tracker, and can additionally or alternatively receive input respective of the eye position and orientation from the eye tracker. For example, the eye/head position and orientation can be determined using proximity sensors, cameras, structured illumination, time-of-flight, placing a marker on the user head or eyes (e.g., visual, magnetic or RF marker) or any other method.

Adjustable eyepiece system 1000 can be activated automatically based on the sensors installed in the system or based on user activation. The user can activate using voice, keyboard, joystick (of any type), head/eye gesture, control panel etc. The eyepiece can be a non-see through based on micro-display (e.g., OLED, LCOS, LCD or any other). In this case a micro display is coupled to relay optics projecting the image to the user eyes. This can be made using mirrors to fold the optics for ergonomics improvement or obstruction prevention. The eyepiece can be a see-through based on optical combiner, waveguide or projection optics.

In accordance with an alternative embodiment of the disclosed technique, adjustable eyepiece system 1000 aligns eyepieces 1024 to a reference plane, which is orthogonal to the face of the user (as determined by the head tracker). Thus, dynamic eyepiece system 1000 eliminates different alignment of the eyepiece when the user eyes are directed to different places.

4 Trackers & LOS

Referring back to FIG. 2, in some embodiments of the disclosed technique, HMD 208 is coupled with tracker 218 (e.g., tracking the head, the eye, or both). Tracker 218 tracks the LOS of the user (i.e., also referred to as the gaze direction). For example, tracker 218 is an eye tracker directly tracking the user LOS, or is a head tracker tracking the head of the user and accordingly determining the viewer LOS. The LOS can be calculated, for example, for three coordinates (e.g., azimuth, elevation and rotation-orientation) or for six coordinates (position and orientation).

Processing device 206 receives the gaze direction from tracker 218 and accordingly determines the ROI of the operated area respective. That is, the tracked gaze direction serves as an input indicating the ROI, and accordingly processing device 206 produces ROI image sequences from the acquired operated-area sequences by cropping the respective portion of the ROI and resizing the image sequences to fit HMD 208.

Tracker 218 can be, for example, an optical tracker employing at least one image sensor and at least three optical markers. For instance, the sensor can be mounted on the head of the user and the markers on the bed of the patient. Alternatively, the sensor is mounted on the bed of the patient (or at another place in the OR), and the markers are mounted on the head of the user. Further alternatively, one sensor is mounted on the head and one in the OR and some markers are mounted on the head and some in the OR. Alternatively, tracker 218 can be electromagnetic tracker, ultrasonic tracker, electromechanical tracker (e.g., Micro-electro-mechanical System-MEMS-gyroscopes), and any other tracking mechanism.

Tracker 218 can either calculate the user LOS, or gather data enabling processing device 206 to calculate the LOS. As mentioned above, the user LOS can be employed as input for indicating which region of the operated area is of interest to the user, thereby allowing processing device to determine the ROI, and accordingly to produce respective ROI image sequences. The LOS (and possibly the position or location of the user head) can be employed for other (or additional) functions and applications of microsurgery system 200, as would be exemplified in the following paragraphs.

Tracking the viewer LOS enables processing device 206 to create space-stabilized objects within the display. In other words, HMD 208 utilizes the tracked LOS for constantly presenting symbols, information and images, in the same location within the field of regard of the user. The space-stabilized objects can include the image sequences from cameras 202 and 204, and any further data that may be useful to the user, such as medical history, previously obtained medical imaging data (e.g., CT or MRI scans), current patient vital statistics (e.g., pulse and blood pressure), and the like. These may be placed at user-defined spatial locations. For example, looking at 45° to the left, the user can see the patient's last CT scan, looking forward gives the ROI magnified image sequences, looking down allows to see the patient through the see-through display, and looking up provides the time display. For many users, the ability to provide a stable image helps to prevent nausea.

Tracker 218 can be employed for controlling the brightness of a see-through display. For example, when the user's head is in one direction the transparency is low, so the projected image contrast is high. When the head moves to another direction, the transparency is high, so the user can view other portion of the OR clearly, thereby increasing the situational awareness of the user. The display brightness reduction can also be used to improve the contrast of a background image.

According to the LOS of the viewer a see-through HMD can focus the projected image according to the real world object distance. With additional mechanism (e.g., a camera) and the LOS of the viewer the HMD can detected the distance to the object and focus accordingly. This focus mechanism will prevent fatigues to the eye (due to changes in focus between the display and the real world).

Tracker 218 can be used as an input interface for controlling various functions. Tracker 218 can be employed for controlling the digital image magnification. Zoom control can be performed by moving the head forward and backward, setting the "zoom in" and "zoom out" function. Tracker 218 can be employed for controlling the movements of the cameras (in case the cameras are moveable). For example, the cameras are enslaved to the head motions.

An eye tracker can be used to locate the exact eye LOS relative to HMD 208. For example, in case HMD 208 displays a central high resolution image and peripheral lower resolution images, as detailed herein below with reference to FIGS. 9A-9C, the central high resolution image is projected along the eye LOS.

5 Applications

Referring back to FIG. 2, the operated-area image sequences can be used for different applications, as would be exemplified in the following paragraph. The entire data can be saved for late debrief. During the operation, a plurality of users can each select a different ROI (e.g., different coordinates and magnification). Processing device 206 may be configured to apply different image processing or video processing algorithms to different ROI sequences presented to different users. In this manner, each user may select his ROI, and receive a tailored processed ROI image by applying the image processing algorithms or any other operation applied to the user-specific ROI sequence. This is important, as an example, for complicated surgeries, where several surgeons are operating at the same time. Not only surgeons can use the different ROI sequences, but also students, nurses or other staff members, and users which are not in the same operating room. Some ROI sequences can be produced for processing device 206 itself, and not for a human user. For example, the user marks an area of interest which processing device 206 tracks for determining whether there is blood flow or other defined event. The user can mark different ROIs with bookmarking. In this case the user can return to the bookmarked ROI. Bookmarked ROIs can include magnifications change and XY translations.

Processing device 206 can further process the acquired image sequences. For example, processing device 206 can combine the image sequences into a stereoscopic sequence or a 3D video. Processing device 206 can perform other image processing operations, such as image correction (e.g., fixed pattern noise corrections, color corrections, distortion corrections, histogram enhancement and the like), adding markers on relevant image fixtures, tracking objects, emphasizing objects and the like, overlaying monitoring data or patient history data, fusing the image sequences with data gathered by other imaging devices (e.g., CT and MRI).

Processing device 206 can generate different markers of interest features on the projected image sequences. The markers can be employed to specify features to address, such as medical tools and physiological sites. Additionally, processing device 206 can generate important OR equipment data and patient history information to present on the projected display of HMD 208. For example, processing device 206 can overlay monitoring data or patient history data, or fuse the acquired image sequences with other imaging device like CT, MRI and the like. The data can be presented on the displayed sequences or in the field of regard.

Another processing application of processing device 206 is generating a 3D model of the object. It can be made at real-time for fixed cameras or non-real-time for moving cameras. As example, the use for this embodiment can be render of 3D model of the head and brain for neurosurgery (visible area by the cameras). The 3D model can be generated from stereoscopic imagery. In this way a 3D data base on the imaged object is made by using 2 or more fixed cameras imaging the same object from different angles. Another method for 3D image reproduction from 1 camera or more can be time based. The camera (or cameras) is moved to different locations around the subject head. The images are saved in the memory unit as well as their position when capturing the images. Processing device 206 uses the images to generate 3D model of the head and brain based on the captured images from different angles. An exemplary algorithm for such 3D model can be implemented using Radon transform or standard stereoscopic algorithm. This model can be used during the surgery to help the surgeon navigate or improve the 3D orientation. The 3D database can also be used for non-display purpose, such as image correlation, tracking and the like.

Another processing application of processing device 206 is providing guidance to the user. Processing device 206 produces and displays a path for a surgical tool to a selected destination. The path can be generated automatically, manually or by a combination of both. The path is produced by employing the 3D database created from images received from the cameras. Based on the 3D images the microsurgery system of the disclosed technique tracks the tool and guides the surgeon to the designated direction. System 200 can generate warning when the surgeon does not move the tool in right direction or gets close to sensitive areas.

Communication interface 220 is employed for communicating with a remote site 222. For example, processing device 206 can receive data such as the medical history of the patient from the patient's regular clinic. Processing device 206 can send the captured video images to a remote site at which an expert is positioned so that the expert can counsel the medical staff in real-time.

5.1 Virtual Depth of Field

Depth of Field (DOF) of an optical system is a function of many parameters, such as the focal length and the F number. Objects within the DOF are viewed sharply as focused objects, and objects outside the DOF may be blurred. In conventional imaging systems as known in the art, the user may adapt the DOF for her needs. For example, the user can design an optical system having a large DOF in order to focus as many features as possible. Conversely, the user may design a system having a small DOF to allow the user to focus her attention to limited features in the scene. As mentioned above, the microsurgery system of the disclosed technique acquires operated-area image sequences of the operated area. The microsurgery system can present different cropped and resized portions of the operated-area sequences (i.e., ROI sequences) to different viewers. Each user may want to focus on different objects within the displayed image (i.e., each user may require a different DOF).

As detailed above with reference to FIG. 2, microsurgery system 200 includes two cameras 202 and 204 and processing device 206. Cameras 202 and 204 capture image sequences of an operated area from two different perspectives to be displayed to each eye, providing 3D imaging. Processing device 206 can calculate the depth data of various features (or objects) in the 3D image. Using the calculated depth data system 200 can create a virtual DOF (i.e., a sub-region within the real optical DOF) by virtually rendering different parts of the image such that features within the virtual DOF appear in focus, and features outside the virtual DOF appear as blurred, or are otherwise rendered to be seen as background. As an example, in cornea surgery, microsurgery system 200 can blur all the areas in the image which are not the user tools and the thin cornea.

Processing device 206 can determine depth data of different features in the images acquired by cameras 202 and 204, in real-time, by employing techniques, such as stereo imaging algorithms, structured light techniques, time of flight algorithms, and the like. Processing device 206 can determine the depth data of features in the images, not in real-time, by employing techniques, such as by changing the focus on consecutive images and labeling the distances of the features.

The virtual DOF (i.e., the range of distances at which objects would appear as in focus, or the objects of interests which would appear as in focus) may be set in various ways, such as manually; automatically by the microsurgery system according to a predefined goal, or according to a value that is set according to a cuing process performed by the user; automatically by a learning process that identifies the existing motion-box of objects in the scene when the system is performing its normal functions, or during a specified learning period.

Once the virtual DOF is set, objects (or features) within the image presented to the user can be manipulated according to their respective depth, and the set virtual DOF. The manipulations are based on image processing techniques. For example, objects outside of the virtual DOF can be blurred, blackened, erased, the transparency of objects outside the virtual DOF can be increased, and the like. In general, any visual manipulation can be employed on the objects for focusing the attention of the user to the objects within the virtual DOF and for rendering the objects outside the virtual DOF to appear as background or as insignificant.

In accordance with another embodiment of the disclosed technique, surgical tools can be displayed in focus even if they are located out of the selected virtual FOV. This is done by tracking the tools and keeping them in focus, regardless of their relative location with respect to the defined virtual DOF.

The virtual DOF of the disclosed technique can be employed for negating some of the problems associated with stereoscopic imaging of microsurgeries. For example, the difference depth of an object in the different cameras can cause hyper-stereopsis on parts of the image. The depth variation of objects may cause difference parallax (or offset) and unnatural stereo image, and may cause squinting, headaches and fatigue for the user. The virtual DOF decreases these stereo issues. The user (or the system) defines the objects of interest in the scene, and the remaining objects are blurred to prevent stereo-related fatigue.

Figure 11B:
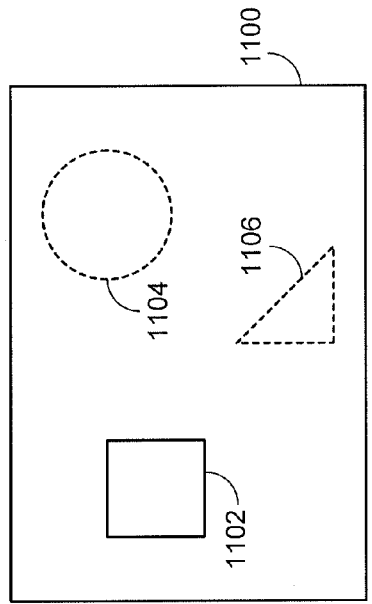
FIGS. 11A, 11B, 11C and 11D, are schematic illustrations of a virtual depth of field scheme for presenting to a user a selected virtual depth of field, operative in accordance with yet another embodiment of the disclosed technique.
Figure 11D:
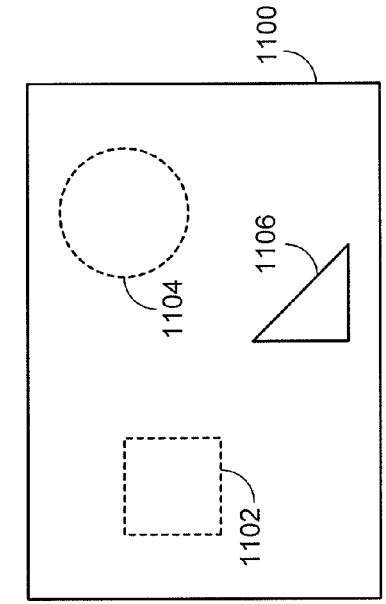
Figure 11A:
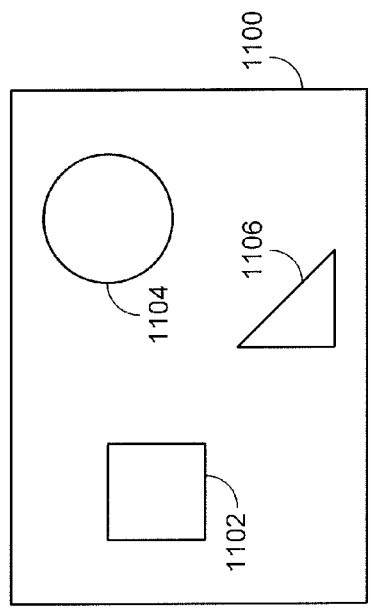
Figure 11C:
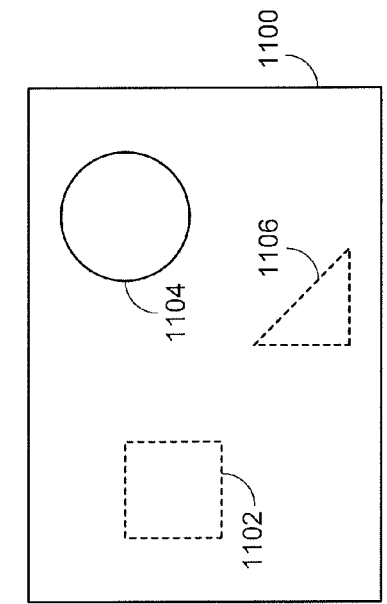

Reference is now made to FIGS. 11A, 11B, 11C and 11D, which are schematic illustrations of a virtual depth of field scheme for presenting to a user a selected virtual depth of field, operative in accordance with yet another embodiment of the disclosed technique. FIG. 11A presents an image of three objects. FIG. 11B presents the image of FIG. 11A in which the first object is within the virtual depth of field and the second and third objects are not. FIG. 11C presents the image of FIG. 11A in which the second object is within the virtual depth of field and the first and third objects are not. FIG. 11D presents the image of FIG. 11A in which the third object is within the virtual depth of field and the first and second objects are not.

With reference to FIG. 11A, an image 1100 includes a first object 1102, a second object 1104 and a third object 1106, depicted as a square, circle and triangle, respectively. A user viewing image 1100 may want to focus her attention to one of the objects. In conventional imaging systems as known in the art, the user would adjust the focus of the imaging system such that the object in which she is interested is in focus and the rest of the image may be blurred. That is, the user would adjust the focus of a conventional imaging system such that the object of interest is within the depth of field of the conventional imaging system. The microsurgery system of the disclosed technique can produce a virtual depth of field, such that the object of interest would be in focus and other objects within the actual, optical, DOF would be blurred. Put another way, the microsurgery system of the disclosed technique would blur all objects in the image, except the object of interest, thereby, focusing the user attention to the object of interest and avoiding confusion and disturbing visual stimulations.

With reference to FIG. 11B, first object 1102 is presented in focus (i.e., depicted as solid line), and second and third objects 1104 and 1106 are presented as blurred (i.e., depicted as dotted lines). With reference to FIG. 11O, second object 1104 is presented in focus (i.e., depicted as solid line), and first and third objects 1102 and 1106 are presented as blurred (i.e., depicted as dotted lines). With reference to FIG. 11D, third object 1106 is presented in focus (i.e., depicted as solid line), and first and second objects 1102 and 1104 are presented as blurred (i.e., depicted as dotted lines).

As mentioned above, each user can be presented with a different image with a different virtual DOF. For example, a first surgeon would view the image of FIG. 11B in which object 1102 is within the virtual DOF, and a second surgeon would view the image of FIG. 11D in which object 1106 is within the virtual DOF. Thereby, each user focuses its attention on relevant image features, such as the tissues she is operating on, and her surgical tool.

6 Additional Inputs for Display

Referring back to FIG. 2, medical imaging source 210 provides medical imaging data to processing device 206. The medical imaging data can be overlaid on the image sequences provided by cameras 202 and 204. For example, medical imaging data can be obtained by CT or MRI scans, ultrasonic imaging, X-ray imaging, infrared imaging, fluoroscopic imaging, and the like. Medical file data source 212 provides processing device 206 with data from the medical file of the patient. Thereby, the processing device can present to the medical staff the history data of the patient. Physiological measures source 214 can include various sensors for determining various physiological measures of the patient, such as the vital signs (e.g., body temperature, pulse rate, blood pressure and respiratory rate), and other physiological measures such as EEG, and the like. Processing device 206 may be further communicating with additional units within the OR (e.g., microscopes, laparoscopes, endoscopes).

It is noted that the microsurgery system described herein above can be employed for every micro-medical procedure in an operating room or in any other treatment room. Some examples of such procedures include imaging in the area of orthopedic micro-surgery, gynecological micro-surgery, otolaryngology, neurosurgery, oncologic micro-surgery, pediatric, oral and maxillofacial, plastic micro-surgery, and the like. In the above description, another embodiment is an example or implementation of the invention. The various appearances of "one embodiment", "an embodiment" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment.

The invention claimed is:

1. A microsurgery system comprising:
a head mounted display (HMD) configured to display to a user in real-time magnified image sequences of a region of interest (ROI) of an operated area;
at least one camera configured to acquire operated-area image sequences of said operated area, a size of said operated area being larger than a size of said ROI, said at least one camera being suspended above said operated area and being mechanically and optically disconnected from said HMD;
a memory configured to store said operated-area image sequences; and
a processing device coupled with said HMD, said at least one camera and with said memory, said processing device being configured to receive an input indicating said ROI, and configured to produce said magnified image sequences of said ROI from said operated-area image sequences;
wherein said HMD displays said magnified image sequences of said ROI to said user at an angular resolution which is equal to or smaller than the angular resolution of a human eye.

2. The microsurgery system according to claim 1, wherein said processing device is configured to grab a full image out of a sensor of said at least one camera, and to digitally crop and resize said ROI.

3. The microsurgery system according to claim 1, wherein said processing device is configured to grab said ROI out of a sensor of said at least one camera by at least one of the list consisting of:
addressing only pixels corresponding to said ROI; and
under-sampling said sensor.

4. The microsurgery system of claim 1, further comprising a tracker configured to track a line of sight (LOS) of said user, wherein said processing device is configured to determine said ROI according to said LOS.

5. The microsurgery system according to claim 4, wherein said tracker is an eye tracker.

6. The microsurgery system according to claim 4, wherein said image sequences of said ROI are modified at least partially based on spatial movements of said HMD as detected by said tracker.

7. The microsurgery system according to claim 1, wherein said at least one camera is configured to carry out automatic focus based on said ROI.

8. The microsurgery system according to claim 1, further comprising an array of controllable light sources facing said operated-area, and wherein said controllable light sources are dynamically adjusted based on a dynamic analysis of an image histogram of said image sequences to achieve at least one effect selected from:
reduce specular reflections; and
increase the dynamic range of the captured scene by of said at least one camera.

9. The microsurgery system according to claim 1, wherein said HMD includes a first region and a second region, an angular resolution of said first region being numerically smaller than 0.000582 radians and an angular resolution of said second region being numerically larger than that of said first region, and wherein said first region has a field of view of at least 2° and is substantially centered around said LOS of said user.

10. The microsurgery system of claim 1, wherein said processing device crops a ROI portion of said operated-area image sequences respective of said ROI, and resizes said ROI portion for producing said magnified image sequences of said ROI.

11. The microsurgery system of claim 1, wherein said at least one camera includes two image sensors, and further includes a folding optical system located in front of said two image sensors, said folding optical system including at least a pair of fixed mirrors and a pair of moveable mirrors, wherein at least one of said moveable mirrors is configured to move away and toward another one of said fixed mirrors.

12. The microsurgery system of claim 1, wherein each of said movable mirrors is configured to move toward and away from another one of said moveable mirrors, and wherein each of said movable mirrors is configured to rotate about an axis perpendicular to an optical axis of said microsurgery system and perpendicular to an axis extending between said movable mirrors, thereby said movable mirrors enable said microsurgery system to adjust a parallax of an object in an image acquired by a first one of said image sensors and an image acquired by a second one of said image sensors.

13. The microsurgery system of claim 1, wherein said at least one camera includes an image sensor, a secondary sensor and a beam splitter directing light from said operated area toward said image sensor and toward said secondary image sensor.

14. The microsurgery system of claim 1, further including a robotic arm, wherein said at least one camera is mounted on said robotic arm.

15. The microsurgery system of claim 14, wherein said robotic arm is enslaved to a LOS of said HMD.

16. The microsurgery system of claim 14, wherein said robotic arm is enslaved to a medical tool operated by said user.

17. The microsurgery system of claim 1, further comprising a focus-control 2D sensor array configured to receive an image captured by a selected one of said at least one camera, said focus-control sensor being tilted with respect to an optical axis of said at least one camera, wherein said processing device is configured to determine a location in said focus-control sensor in which an image is focused, and accordingly to adjust focus characteristics of said selected one of said at least one camera.

18. The microsurgery system of claim 1, further comprising a subcutaneous imaging module including an infrared (IR) light source, a first optical transform system, a second optical transform system, a spatial frequency filter and an image sensor, said spatial frequency filter being located between said first optical transform system and said second optical transform system and said image sensor is located after said second optical transform system, wherein said IR light source illuminates said operated area, said first optical transform system is configured to transform an IR image of said operated area into a frequency image of said operated area, said spatial frequency filter being configured to direct selected frequencies of said frequency image toward said second optical transform system, said second optical transform system being configured to transform said frequency image back into said operated area image.

19. The microsurgery system according to claim 1, wherein said HMD is a see-through display.

20. The microsurgery system of claim 19, wherein said HMD includes a shutter configured for controlling a transparency of at least a portion of said HMD see through display.

21. The microsurgery system of claim 20, wherein said shutter is configured to automatically change said transparency according to orientation and/or position changes of said HMD.

22. The microsurgery system of claim 1, wherein said processing device is configured to determine a virtual Depth of Field (DOF) out of a DOF of said at least one camera, said processing device being configured to determine which elements of said operated area image sequences are out of said virtual DOF, and wherein said processing device is configured to blur said elements of said operated area image sequences that are out of said virtual DOF.

23. The microsurgery system of claim 1, further comprising an OCT module.

24. The microsurgery system of claim 1, further comprising a light source for illuminating said operated area, wherein said light source is configured to transmit light pulses according to a selected time scheme, and wherein said at least one camera is synchronized with said time scheme of said light source.

25. The microsurgery system of claim 1, further comprising an additional HMD, wherein said processing device is further configured to produce additional magnified image sequences of an additional ROI from said operated-area image sequences, and wherein said additional HMD is configured to display to an additional user in real time said additional magnified image sequences of said additional ROI.

26. The microsurgery system of claim 1, wherein said processing device is further configured to produce a Three Dimensional (3D) model of said ROI from said operated-area image sequences.

27. The microsurgery system of claim 1, further comprising at least two light sources, each of said at least two light sources being configured to produce illumination at a respective spectral band.

28. The microsurgery system of claim 1, wherein said at least one camera is configured to operate without an optical zoom mechanism.

29. The microsurgery system of claim 1, further comprising a lighting system including a light source and a shutter module, said shutter module being positioned between said light source and said operated area, said light source being configured to produce an illumination beam for illuminating said operated area, said shutter module being configured for selectively attenuating spatial portions of said illumination beam.

30. A method for displaying in real time magnified digital image sequences of an operated area, the method comprising the following procedures:
  acquiring operated-area image sequences of said operated area from a viewpoint suspended above said operated area;
  receiving an input indicating a region of interest (ROI) of said operated area, a size of said operated area being larger than a size of said ROI;
  producing magnified image sequences of said ROI from said operated-area image sequences; and
  displaying in real-time said magnified image sequences of said ROI to a line of sight (LOS) of a user, wherein said magnified image sequences of said ROI are displayed to said user at an angular resolution which is equal to or smaller than the angular resolution of a human eye;
  wherein said LOS of said user is independent of said viewpoint.

* * * * *